United States Patent
Ray et al.

(10) Patent No.: US 11,937,925 B2
(45) Date of Patent: *Mar. 26, 2024

(54) SYSTEMS, DEVICES, AND METHODS FOR PERFORMING TRANS-ABDOMINAL FETAL OXIMETRY AND/OR TRANS-ABDOMINAL FETAL PULSE OXIMETRY USING INDEPENDENT COMPONENT ANALYSIS

(71) Applicant: Raydiant Oximetry, Inc., San Ramon, CA (US)

(72) Inventors: Neil Padharia Ray, Sacramento, CA (US); Mark Andrew Rosen, Piedmont, CA (US); Adam Jacobs, Hollis, NH (US); Kenneth Holt, Cacadero, CA (US)

(73) Assignee: Raydiant Oximetry, Inc., San Ramon, CA (US)

( * ) Notice: Subject to any disclaimer, the term of this patent is extended or adjusted under 35 U.S.C. 154(b) by 68 days.

This patent is subject to a terminal disclaimer.

(21) Appl. No.: 17/869,251

(22) Filed: Jul. 20, 2022

(65) Prior Publication Data

US 2022/0354390 A1 Nov. 10, 2022

Related U.S. Application Data

(63) Continuation of application No. 16/958,136, filed as application No. PCT/US2018/068042 on Dec. 28, 2018, now Pat. No. 11,419,530.

(Continued)

(51) Int. Cl.
*A61B 5/1464* (2006.01)
*A61B 5/00* (2006.01)

(Continued)

(52) U.S. Cl.
CPC ........ *A61B 5/1464* (2013.01); *A61B 5/14546* (2013.01); *A61B 5/14552* (2013.01);
(Continued)

(58) Field of Classification Search
CPC .............. A61B 5/1455; A61B 5/14551; A61B 5/14552; A61B 5/1464; A61B 5/1482;
(Continued)

(56) References Cited

U.S. PATENT DOCUMENTS

| 4,911,167 A | 3/1990 | Corenman et al. |
| 5,348,002 A | 9/1994 | Caro |

(Continued)

FOREIGN PATENT DOCUMENTS

| CN | 103381094 A | 11/2013 |
| EP | 1054620 B1 | 1/2010 |

(Continued)

OTHER PUBLICATIONS

Raydiant Oximetry, Inc.; EP Application No. 18896485.2; First Examination Report; dated Oct. 21, 2022; 5 pp.

(Continued)

*Primary Examiner* — Eric F Winakur
(74) *Attorney, Agent, or Firm* — Resonance IP Law, PC

(57) ABSTRACT

Independent component analysis may be performed on a plurality of detected electronic signals to separate signals within the detected electronic signals that are contributed by different sources. Each of the plurality of detected electronic signals may be received from a separate detector and may correspond to a detected optical signal emanating from a pregnant mammal's abdomen and a fetus contained therein. The detected optical signals may correspond to light that is projected into the pregnant mammal's abdomen from a light source. The separated signals may be analyzed to determine a separated signal that corresponds to light incident upon the (Continued)

fetus, which may be analyzed to determine a fetal hemoglobin oxygen saturation level of the fetus. An indication of the fetal hemoglobin oxygen saturation level may then be provided to the user.

29 Claims, 7 Drawing Sheets

Related U.S. Application Data

(60) Provisional application No. 62/611,849, filed on Dec. 29, 2017.

(51) Int. Cl.
| | | |
|---|---|---|
| A61B 5/145 | (2006.01) | |
| A61B 5/1455 | (2006.01) | |
| A61B 5/03 | (2006.01) | |
| A61B 5/08 | (2006.01) | |

(52) U.S. Cl.
CPC .......... *A61B 5/7203* (2013.01); *A61B 5/7225* (2013.01); *A61B 5/033* (2013.01); *A61B 5/08* (2013.01); *A61B 2562/0238* (2013.01); *A61B 2562/046* (2013.01)

(58) Field of Classification Search
CPC ... A61B 5/4362; A61B 5/7203; A61B 5/7225; A61B 5/7235
See application file for complete search history.

(56) References Cited

U.S. PATENT DOCUMENTS

| | | | |
|---|---|---|---|
| 5,807,271 | A | 9/1998 | Tayebi et al. |
| 5,835,558 | A | 11/1998 | Maschke |
| 6,498,942 | B1 | 12/2002 | Esenaliev et al. |
| 6,690,958 | B1 | 2/2004 | Walker et al. |
| 7,047,055 | B2 | 5/2006 | Boas et al. |
| 7,469,158 | B2 | 12/2008 | Cutler et al. |
| 7,515,948 | B1 | 4/2009 | Balberg et al. |
| 7,831,300 | B2 | 11/2010 | Kolluri et al. |
| 8,275,436 | B2 | 9/2012 | Wang et al. |
| 8,275,451 | B2 | 9/2012 | Marossero et al. |
| 8,311,600 | B2 | 11/2012 | Katura et al. |
| 8,644,900 | B2 | 2/2014 | Balberg et al. |
| 9,320,464 | B2 | 4/2016 | Volmer et al. |
| 9,757,058 | B2 | 9/2017 | Ray |
| 9,968,286 | B2 | 5/2018 | Ray |
| 10,362,974 | B2 | 7/2019 | Ray |
| 2003/0073910 | A1 | 4/2003 | Chance |
| 2004/0116789 | A1 | 6/2004 | Boas et al. |
| 2005/0267376 | A1 | 12/2005 | Marossero et al. |
| 2006/0122475 | A1 | 6/2006 | Balberg et al. |
| 2006/0189882 | A1 | 8/2006 | Thomas |
| 2008/0208009 | A1 | 8/2008 | Shklarski |
| 2009/0209874 | A1 | 8/2009 | Kolluri et al. |
| 2009/0281402 | A1 | 11/2009 | Chance |
| 2010/0081901 | A1 | 4/2010 | Buice et al. |
| 2011/0218413 | A1 | 9/2011 | Wang et al. |
| 2012/0190946 | A1 | 7/2012 | Bernreuter |
| 2013/0338460 | A1 | 12/2013 | He et al. |
| 2015/0099950 | A1 | 4/2015 | Al-Ali et al. |
| 2016/0015304 | A1 | 1/2016 | Esenaliev et al. |
| 2016/0128594 | A1 | 5/2016 | Amir et al. |
| 2017/0188920 | A1 | 7/2017 | Ray |
| 2018/0070871 | A1 | 3/2018 | Ray |
| 2019/0343437 | A1 | 11/2019 | Ray |

FOREIGN PATENT DOCUMENTS

| | | |
|---|---|---|
| WO | 2004086966 A1 | 10/2004 |
| WO | 2009032168 A1 | 3/2009 |
| WO | 2017117280 A1 | 7/2017 |
| WO | 2018094391 A3 | 7/2018 |

OTHER PUBLICATIONS

Tamura et al.; Wearable Photoplethysmographic Sensors—Past and Present; Electronics 2014, 3, 282-302; doing:10.3390/electronics3020282; ISSN 2079-9292.

Mawn, et al., "Trans-abdominal Monitoring of Fetal Arterial Oxygen Saturation Using Pulse Oximetry," IEEE EMBS—NEBE, 227-228, 2002.

McNamara, et al., "Continuous intrapartum pH, pO2, pCO2, and SpO2 monitoring," Obstet Gynecol Clin North Am, 26(4): 671-693, Dec. 1999.

Meschia, et al., "A Comparison of the Oxygen Dissociation Curves of the Bloods of Maternal, Fetal and Newborn Sheep at Various pHs," In: Oxgen Dissociation Curves in Sheep at Various pHs, pp. 95-97, Sep. 23, 1960.

Mesquita, et al., "Direct measurement of tissue blood flow and metabolism with diffuse optics," Philosophical Transactions of The Royal Society A, 369: 4390-4403, 2011.

Miller, "Raydiant Oximetry: Provides Crucial Comfort for New Mothers," MedTech Strategist, 5(4), pp. 2, Mar. 27, 2018.

Molavi, et al., "Motion Artifact Removal from Muscle NIR Spectroscopy Measurements," Conference paper in Canadian Conference on Electrical and Computer Engineering, pp. 1-5, May 2010.

Mourant, et al., "Mechanisms of light scattering from biological cells relevant to noninvasive optical-tissue diagnostics," Applied Optics, 37(15): 3586-3593, Jun. 1, 1998.

Nasiriavanaki, et al., "High-resolution photoacoustic tomography of resting-state functional connectivity in the mouse brain," PNAS, 111(1): 21-26, Jan. 7, 2014.

Nelson, et al., "Electronic fetal monitoring, cerebralpalsy, and caesarean section: assumptions versus evidence," BMJ, 355: pp. 1-3, Dec. 1, 2016.

Nioka, et al., "Fetal transabdominal pulse oximeter studies using a hypoxic sheep model," The Journal of Maternal-Fetal and Neonatal Medicine, 17(6): 393-399, Jun. 2005.

Nitzan, et al., "Calibration-Free Pulse Oximetry Based on Two Wavelengths in the Infrared—A Preliminary Study," Sensors 2014, 14: 7420-7434, Apr. 23, 2014.

Nonnenmacher, et al., "Predictive value of pulse oximetry for the development of fetal acidosis," J. Perinat. Med, 38: 83-86, 2010.

Noren, et al., "Reduced prevalence of metabolic acidosis at birth: an analysis of established STAN usage in the total population of deliveries in a Swedish district hospital," American Journal of Obstetrics & Gynecology, 202, pp. 546.e1-546.e7, Jun. 2010.

Novak, et al., "Perinatal Brain Injury Mechanisms, Prevention, and Outcomes," Clin Pernatol, 45: 357-375, 2018.

OBG Project, "Which Fetal Heart Monitoring Parameters Best Predict Fetal Acidemia?," https://www.obgproject.com/category/grandrounds/) pp. 1-2, date unknown.

Office Action dated Feb. 1, 2018, from the Taiwan Intellectual Property Office, for Taiwan Patent Application No. 105143848, 17 pages.

Olutoye, et al., "Food and Drug Administration warning on anesthesia and brain development: implications for obstetric and fetal surgery," American Journal of Obstetrics & Gynecology, pp. 98-102, Jan. 2018.

Patient Safety Movement Foundation, "Actionable Patient Safety Solution (APSS) #11C: Reducing Unnecessary C-Sections," 2018 Patient Safety Movement Foundation, pp. 1-8, Aug. 15, 2018.

PCT International Search Report and the Written Opinion of the International Searching Authority for International Application No. PCT/US2018/068042 dated Apr. 26, 2019.

PCT International Search Report, International Searching Authority, for International Patent Application No. PCT/US2017/062782 filed on Nov. 21, 2017, pp. 1 to 4, dated Feb. 19, 2018.

PCT/US2018/068042 International Search Report and Written Opinion, dated Apr. 26, 2019, 16 pages.

PCT/US2018/068049 International Search Report and Written Opinion, dated Apr. 26, 2019, 20 pages.

Peat, et al., "Continuous intrapartum measurement of fetal oxygen saturation," The Lancet, Jul. 23, 1988, pp. 213.

(56) References Cited

OTHER PUBLICATIONS

Peebles, et al., "Effect of oxytocin on fetal brain oxgenation during labour," The Lancet, 338: 254-255, Jul. 27, 1991.

Peek, et al., "Fetal Pulse Oximetry and Cesarean Delivery," The New England Journal of Medicine, 356: 1377-1378, Mar. 29, 2007.

Pereira, et al., "Recognition of chronic hypoxia and pre-existing foetal injury on the cardiotocograph (CTG): Urgent need to think beyond the guidelines," Porto Biomedical Journal, 2(4): 124-129, 2017.

Peters, et al., "Beat-to-beat detection of fetal heart rate: Doppler ultrasound cardiotocography compared to direct ECG cardiotocography in time and frequency domain," Physiological Measurement, 25: 585-593, 2004.

Phelan, et al., "Fetal Heart Rate Observations in the Brain-Damaged Infant," Seminars in Perinatology, 24(3): 221-229, Jun. 2000.

Philips proprietary camera based monitoring technology is first in the world to measure absolute arterial blood oxygenation (SpO2) levels without ever touching the patient, Jun. 6, 2016, 4 pages (https://www.usa.philips.com/a-w/about/news/archive/standard/news/press/2016/20160606-philips-proprietary-camera-based-monitoring-technology-is-first-in-the-world-to-measure-absolute-arterial-blood-oxygenation-levels-without-ever-touching-the-patient.html) Jun. 6, 2016.

Pifferi, et al., "Real-time method for fitting time-resolved relectance and transmittance measurements with a Monte Carlo model," Applied Optics, 37(13): 2774-2776, May 1, 1998.

Porreco, et al., "Dystocia in nulliparous patients monitored with fetal pulse oximetry," American Journal of Obstetrics and Gynecology, 190: 113-117, 2004.

Ragozzino, et al., "Average Fetal Depth in Utero: Data for Estimation of Fetal Absorbed Radiation Dose," Radiology, 158(2): 513-515, 1986.

Ramanujam, et al., "Antepartum, Transabdominal Near Infrared Spectroscopy: Feasibility of Measuring Photon Migration Through the Fetal Head In Utero," The Journal of Maternal-Fetal Medicine, 8: 275-288, 1999.

Ramanujam, et al., "Photon migration through fetal head in utero using continuous wave, near infrared spectroscopy," Journal of Biomedical Optics, 5(2): 173-184, Apr. 2000.

Rei, et al., "Neurological damage arising from intrapartum hypoxia/acidosis," Best Practice & Research Clinical Obstetrics and Gynaecology, 30: 79-86, 2016.

Ren, et al., "Quasi-simultaneous multimodal imaging of cutaneous tissue oxygenation and perfusion," Journal of Biomedical Optics, 20(12): pp. 121307-1 thru 121307-10, Dec. 2015.

Reuss, "Factors Influencing Fetal Pulse Oximetry Performance," Journal of Clinical Monitoring and Computing, 18: 13-24, 2004.

Reuss, "Multilayer Modeling of Reflectance Pulse Oximetry," IEEE Transactions on Biomedical Engineering, 52(2): 153-159, Feb. 2005.

Reuss, et al., "The pulse in reflectance pulse oximetry: modeling and experimental studies," Journal of Clinical Monitoring and Computing, 18: 289-299, 2004.

Rivolta, et al., "Acceleration and Deceleration Capacity of Fetal Heart Rate in an In-Vivo Sheep Model," PLOS One, 98(8): 1-10, Aug. 2014.

Roche-Labarbe, et al., "Noninvasive Optical Measures of CBV, StO2, CBF Index, and rCMRO2in Human Premature Neonates' Brains in the First Six Weeks of Life," Human Brain Mapping, 31: 341-352, 2010.

Roemer, et al., "Sensitivity, specificity, receiver-operating characteristic (ROC) curves and likelihood ratios for electronic foetal heart rate monitoring using new evaluation techniques," Z Geburtshilfe Neonatol, 214(3): 108-118, Jun. 2010 (Abstract Only).

Ross, "Labor and Fetal Heart Rate Decelerations: Relation to Fetal Metabolic Acidosis," Clinical Obstetrics and Gynecology, 54(1): 74-82, 2011.

Roth, et al., "Unequal Motherhood: Racial-Ethnic and Socioeconomic Disparities in Cesarean Sections in the United States," Social Problems, 59(2): 207-227, May 2012.

Saager, et al., "Direct characterization and removal of interfering absorption trends in two-layer turbid media," J. Opt. Soc. Am. A, 22(8): 1874-1882, Sep. 2005.

Sabiani, et al., "Intra- and interobserver agreement among obstetric experts in court regarding the review of abnormal fetal heart rate tracings and obstetrical management," American Journal of Obstetrics & Gynecology, 213(6): pp. 856.e1 thru 856.e8, Dec. 2015.

Saccone, et al., "Electrocardiogram ST Analysis During Labor A Systematic Review and Meta-analysis of Randomized Controlled Trials," Obstetrics & Gynecology, 127(1): 127-135, Jan. 2016.

Salamalekis, et al., "Computerised intrapartum diagnosis of fetal hypoxia based on fetal heart rate monitoring and fetal pulse oximetry recordings utilising wavelet analysis and neural networks," BJOG: an International Journal of Obstetrics and Gynaecology, 109: 1137-1142, Oct. 2002.

Salamalekis, et al., "Fetal pulse oximetry and wavelet analysis of the fetal heart rate in the evaluation of abnormal cardiotocography tracings," J. Obstet. Gynaecol. Res., 32(2): 135-139, Apr. 2006.

Sartwelle, et al., "A half century of electronic fetal monitoring and bioethics: silence speaks louder than words," Maternal Health, Neonatology, and Perinatology, 3:(21): 1-8, 2017.

Delpy, et al., "Quantification in tissue near-infrared spectroscopy," Phil. Trans. R. Soc. Lond. B, 352: 649-659, 1997.

Dildy, "Fetal Pulse Oximetry," Clinical Obstetrics and Gynecology, 54(1): 66-73, Mar. 2011.

Dildy, et al., "Current status of the multicenter randomized clinical trial on fetal oxygen saturation monitoring in the United States," European Journal of Obstetrics & Gynecology and Reproductive Biology, 72, Suppl. 1, pp. S43-S50, 1997.

Dildy, et al., "Intrapartum fetal pulse oximetry: Fetal oxygen saturation trends during labor and relation to delivery outcome," Am. J. Obstet. Gynecol., 171(3): 679-684, Sep. 1994.

Dildy, et al., "Intrapartum fetal pulse oximetry: Past, present, and future," American Journal of Obstetrics & Gynecology, 175(1): 1-9, Jul. 1996.

Dildy, et al., "Management of prolonged decelerations," OBG Management, 7 pgs., Nov. 2006.

Dildy, et al., "Preliminary Experience with Intrapartum Fetal Pulse Oximetry in Humans," Obstetrics and Gynecology, 81(4): 630-635, Apr. 1993.

Diniz, In Adaptive Filtering Algorithms and Practical Implemetation, Springer, Third Edition, pp. 636, 2008.

Dong, et al., "Simultaneously Extracting Multiple Parameters via Fitting One Single Autocorrelation Function Curve in Diffuse Correlation Spectroscopy," IEEE Transactions on Biomedical Engineering, 60(2): 361-368, Feb. 2013.

Donlon, et al., "MEG Visual Stimuli Software," MEG Setup Documentation, pp. 3.

Durduran, et al., "Diffuse correlation spectroscopy for non-invasive, micro-vascular cerebral bloodflow measurement," NeuroImage, 85: 51-63, 2014.

Durduran, et al., "Diffuse optics for tissue monitoring and tomography," Reports on Progress in Physics, 73, pp. 44, 2010.

East, et al., "A cost-effectiveness analysis of the intrapartum fetal pulse oximetry multicentre randomised controlled trial (the FOREMOST trial)," BJOG An International Journal of Obstetrics and Gynaecology, pp. 1080-1087, 2006.

East, et al., "Fetal oxygen saturation and uterine contractions during labor," Am J Perinatol, 15(6): 345-349, Jun. 1998 (Abstract Only).

East, et al., "Fetal oxygen saturation during maternal bearing down efforts in the second stage of labor," Am J. Perinatol, 15(2): 121-124, 1998 (Abstract Only).

East, et al., "Fetal Oxygen Saturation Monitoring in Labour: An Analysis of 118 Cases," Aust. and NZ Journal of Obstetrics and Gynaecology, 37(4): 397-401, 1997.

East, et al., "Fetal pulse oximetry for fetal assessment in labour (Review)," The Cochrane Collaboration, pp. 76, 2014.

East, et al., "Intrapartum fetal scalp lactate sampling for fetal assessment in the presence of a non-reassuring fetal heart rate trace (Review)," The Cochrane Database of Systematic Reviews 2015, Issue 5. Art. No. CD006174, pp. 39, 2015.

East, et al., "Intrapartum Oximetry of the Fetus," Anesthesia & Analgesia, 105(6), pp. S59-S65, Dec. 2007.

(56) References Cited

OTHER PUBLICATIONS

East, et al., "The effect of intrapartum fetal pulse oximetry, in the presence of a nonreassuring fetal heart rate pattern, on operative delivery rates: A multicenter, randomized, controlled trial (the FOREMOST trial)," American Journal of Obstetrics and Gynecology, 194, pp. 606.e1-606.e16, 2006.

East, et al., "Update on intrapartum fetal pulse oximetry," Aust NZ J Obstet Gynaecol, 42(2): 119-124, 2002.

Eden, et al., "Reengineering Electronic Fetal Monitoring Interpretation: Using the Fetal Reserve Index to Anticipate the Need for Emergent Operative Delivery," Reproductive Sciences, 25(4): 487-497, 2018.

Eden, et al., "The "Fetal Reserve Index": Re-Engineering the Interpretation and Responses to Fetal Heart Rate Patterns," Fetal Diagnosis and Therapy, 43: 90-104, Jun. 2017.

Emberson, et al., "Isolating the effects of surface vasculature in infant neuroimaging using short-distance optical channels: a combination of local and globaleffects," Neurophotonics, 3(3), pp. 031406-1-031406-12, Jul.-Sep. 2016.

Eunson, "The long-term health, social, and financial burden of hypoxic-ischaemic encephalopathy," Developmental Medicine & Child Neurology, 57 (Suppl. 3): 48-50, 2015.

Evans, et al., "Re-engineering the interpretation of electronic fetal monitoring to identify reversible risk for cerebral palsy: a case control series," The Journal of Maternal-Fetal & Neonatal Medicine, pp. 10, 2018.

Fabbri, et al., "Optical measurements of absorption changes in two-layered diffusive media," Physics in Medicine & Biology, 49: 1183-1201, Mar. 18, 2004.

Fantini, et al., "Frequency-domain multichannel optical detector for nonivasive tissue spectroscopy and oximetry," Optical Engineering, 34(1): 32-42, Jan. 1995.

Fantini, et al., "Frequency-domain techniques for tissue spectroscopy and imaging", In Handbook of Optical Biomedical Diagnostics, Second Edition, vol. 1: Light Tissue Interaction, Chapter 7, pp. 1-52, 2002.

Farrell, et al., "Influence of layered tissue architecture on estimates of tissue optical properties obtained from spatially resolved diffuse reflectometry," Applied Optics, 37(10): 1958-1972, Apr. 1, 1998.

Farzam, "Hybrid diffuse optics for monitoring of tissue hemodynamics with applications in oncology," Doctoral Thesis in Photonics, Institute of Photonic Sciences, pp. 240, Jul. 2014.

Fatemi, et al., "Hypoxic Ischemic Encephalopathy in the Term Infant," Author manuscript; available in PMC, Dec. 1, 2010, pp. 23, 2009.

Figures of Two-minute tracing showing fetal heart rate, and Pulse oximetry tracing from 25-week gestation fetus undergoing open congenital diaphragmatic hernia repair, Anesthesia for Fetal Procedures and Surgery, pp. 280-281.

Firbank, et al., "An investigation of light transport through scattering bodies with non-scattering regions," Phys. Med. Biol., 41: 767-783, 1996.

Fong, D.D., et al., "Contextually-aware Fetal Sensing in Transabdominal Fetal Pulse Oximetry," 2020 ACM/IEEE 11th International Conference on Cyber-Physical Systems (ICCPS), Apr. 2020.

Fong, D.D., et al., "Optode Design Space Exploration for Clinically-robust Non-invasive Fetal Oximetry," ACM Transactions on Embedded Computing Systems, vol. 18, No. 5s, Article 63, Oct. 2019.

Fong, et al., "Recovering the Fetal Signal in Transabdominal Fetal Pulse Oximetry," Smart Health, 9-10: 23-26, Jul. 9, 2018.

Fong, et al., "Transabdominal Fetal Blood Oximetry," Website of the University of California, Davis, Office of Research, http://research.ucdavis.edu/u/s/ia, pp. 1, 2017.

Fong, et al., "Transabdominal Fetal Pulse Oximetry: The Case of Fetal Signal Optimization," 2017 IEEE 19th International Conference on e-Health Networking, Applications and Services (Healthcom), pp. 6, 2017.

Franceschini, et al., "Assessment of Infant Brain Development with Frequency-Domain Near-Infrared Spectroscopy," Pediatr Res., 61(5): 546-551, 2007.

Franceschini, et al., "Influence of a superficial layer in the quantitative spectroscopic study of strongly scattering media," Applied Optics, 37(31): 7447-7458, Nov. 1, 1998.

Gagnon, et al., "Further improvement in reducing superficial contamination in NIRS using doubleshort separation measurements," NeuroImage, 85: 127-135, 2014.

Gagnon, et al., "Short separation channel location impacts the performance of short channel regression in NIRS," NeuroImage, 59: 2518-2528, 2012.

Ganesan et al., "Diffuse optical spectroscopic imaging of subcutaneous adipose tissue metabolic changes during weight loss," Int J Obes (Lond). Aug. 2016 ; 40(8). Author Manuscript available in PMC Oct. 22, 2016. pp. 1292-1300, Oct. 2016.

Gardner, et al., "Enhanced Umbilical Blood Flow During Acute HypoxemiaAfter Chronic Umbilical Cord Compression, A Role for Nitric Oxide," Basic Science Reports in Circulation, pp. 331-335, Jun. 30, 2003.

Gardosi, et al., "Adaptation of pulse oximetry for fetal monitoring during labour," The Lancet, 337: 1265-1267, May 25, 1991.

Gardosi, et al., "Continuous Intrapartum Monitoring Offectal Oxygen Saturation," The Lancet, Sep. 16, 1989, pp. 692-693.

Garite, et al., "Transactions of the Twentieth Annual Meeting of the Society for Maternal-Fetal Medicine—Continued," American Journal of Obstetrics and Gynecology, 183(5): 1049-1058, Nov. 2000.

Ghiasi, et al., "Transabdominal Fetal Oximetry, Project conducted at the Laboratory for Embedded and Programmable Systems," (LEPS), pp. 1-4.

Giordano, "New ANSI guidelines remind users to take stock of industrial laser protections," Laser Focus World, 50(10):41-43+47 • Oct. 2014.

Sartwelle, et al., "The Ethics of Teaching Physicians Electronic Fetal Monitoring: And Now for the Rest of the Story," Surg J, 3: pp. e42 thru e-47, 2017.

Sassaroli, et al., "Comment on the modified Beer-Lambert law for scattering media," Physics in Medicine & Biology, 49(14): pp. N255 thru N257, Jul. 5, 2004.

Schiermeier, et al., "Sensitivity and specificity of intrapartum computerised FIGO criteria for cardiotocography and fetal scalp pH during labour: multicentre, observational study," BJOG An International Journal of Obstetrics and Gynaecology, pp. 1557-1563, Aug. 26, 2008.

Schweiger, et al., "Near-infrared imaging: photon measurement density functions," Proc. SPIE, 2389: 366-377, May 30, 1995.

Seelbach-Göbel, et al., "The prediction of fetal acidosis by means of intrapartum fetalpulse oximetry," American Journal of Obstetrics and Gynecology, 180(1): 73-81, Jan. 1999.

Severinghaus, et al., "History of Blood Gas Analysis. VII. Pulse Oximetry," Journal of Clinical Monitoring, 3(2): 135-138, Apr. 1987.

Shang, et al., "Portable optical tissue flow oximeter based on diffuse correlation spectroscopy," Optics Letters, 34(22): 3556-3558, Nov. 15, 2009.

Siristatidis, et al., "Alterations in Doppler velocimetry indices of the umbilical artery during fetal hypoxia in labor, in relation to cardiotocography and fetal pulse oximetry findings," Arch Gynecol Obstet, 272: 191-195, 2005.

Siristatidis, et al., "Evaluation of fetal intrapartum hypoxia by middle cerebral and umbilical artery Doppler velocimetry with simultaneous cardiotocography and pulse oximetry," Arch Gynecol Obstet, 270: 265-270, 2004.

Siristatidis, et al., "Intrapartum Surveillance of IUGR Fetuses with Cardiotocography and Fetal Pulse Oximetry," Biology of the Neonate, 83: 162-165, 2003.

Spector-Bagdady, et al., "Clinician Self-Interestand the Case of Electronic Fetal Monitoring," Hastings Center Report, pp. 16-24, Nov.-Dec. 2017.

Spencer, et al., "MASS Spectrometer System for Continuous Skin-Surface and Intravascular Blood Gas Measurement of Maternal-Fetal Respiration in Labour," Journal of Biomedical Engineering, 9: 161-168, Apr. 1987.

Spong, et al., "Preventing the First Cesarean Delivery: Summary of a Joint Eunice Kennedy Shriver National Institute of Child Health and Human Development, Society for Maternal-Fetal Medicine, and

(56) References Cited

OTHER PUBLICATIONS

American College of Obstetricians and Gynecologists Workshop," American Journal of Obstetrics and Gynecology, 120(5): 1181-1193, 2012.
Steinbrink, et al., "Illuminating the BOLD signal: combined fMRI-fNIRS studies," Magnetic Resonance Imaging, 24: 495-505, 2006.
Stipcevic et al., "Characterization of a novel avalanche photodiode for single photon detection in VIS-NIR range," Optics Express, 18(16): 17448-17459, Jul. 30, 2010.
Strangman, et al., "Factors affecting the accuracy of near-infrared spectroscopy concentration calculations for focal changes in oxygenation parameters," NeuroImage, 18: 865-879, 2003.
Subramaniam, "An IR Muscle Contraction Sensor", Cornell University, student project (last modified Jun. 10, 2014), retrieved from: https://people.ece.cornell.edu/land/courses/eceprojectsland/STUDENTPROJ/2013to2014/ras578/Writeup/An%20IR%20Muscle%20Contraction%20Sensor.html, 6 pgs., Feb. 2017.
Sutin, et al., "Time-domain diffuse correlation spectroscopy," Optica, vol. 3, Issue 9, pp. 1006-1013, Sep. 2016.
Tamborini, et al., "Development and characterization of a multi distance and multi wave length diffuse correlation spectroscopy system," Neurophoton, 5(1), pp. 011015-1 thru 011015-10, Jan.-Mar. 2018.
Themelis, et al., "Near-infrared spectroscopy measurement of the pulsatile component of cerebral blood flow and volume from arterial oscillations," Journal of Biomedical Optics, 21(1), pp. 1-15, 2007.
Tomich, "Fetal heart rate monitoring," Power Point—Department of Obstetrics and Gynecology, University of Nebraska College of Medicine, (uploaded Jul. 30, 2014) 69 pages.
Torbenson, et al., "Intrapartum factors associated with neonatal hypoxic ischemic encephalopathy: a case-controlled study," BMC Pregnancy and Childbirth, 17(415): 1-7 , 2017.
Townsend, et al., "Pulse Oximetry," Medical Electronics, Michaelmas Term, 2001.
Truven Health Analytics, The cost of having a baby in the United States,: Truven Health Analytics Marketscan® Study, pp. 1 to 84, 2014.
Truven Health Analytics, The Cost of Having a Baby in the United States—Executive Summary, Truven Health Analytics Marketscan Study, pp. 5, Jan. 2013.
Tu, et al., "An Analytical Model for Optimization of Frequency-domain System," Bioengineering Conference, 2002. Proceedings of the IEEE 28th Annual Northeast, pp. 79-80, 2002.
Uchida, et al., "Reevaluation of intrapartum fetal monitoring using fetaloximetry: A review," The Journal of Obstetrics and Gynaecology Research, pp. 1-8, 2018.
Ultman, et al., "Differential Pathlength Factor for Diffuse Photon Scattering Through Tissue by a Pulse-Response Method," 107: 73-82, 1991.
Valverde, et al., "Effectiveness of pulse oximetry versus fetal electrocardiography for the intrapartum evaluation of non reassuring fetal heart rate," European Journal of Obstetric and Gynecology and Reproductive Biology, 159: 333-337, 2011.
Van 'T Hooft, In "Improving evaluation of obstetric interventions," University of Amsterdam Dissertation, pp. 1-243, 2016.
Verkruysse, et al., "Calibration of Contactless Pulse Oximetry," Anesthesia & Analgesia, 124(1): 136-145, Jan. 2017.
Vidaeff, et al., "Fetal pulse oximetry: 8 vital questions," OBG Management, pp. 28-44, Mar. 2004.
Vintzileos, et al., "Transabdominal fetal pulse oximetry with near-infrared spectroscopy," American Journal of Obstetrics and Gynecology, 192: 129-133, 2005.
Vishnoi et al., "Photon migration through fetal head in utero using continuous wave, near-infrared spectroscopy: development and evaluation of experimental and numerical models", J. Biomedical Optics 5(2): 163-172, Apr. 2000.
Weyrich, et al., "Development of a Phantom to Modulate the Maternal and Fetal Pulse Curve for Pulse Oximetry Measurements," Biomed Tech 57 (Suppl. 1): 803-806, 2012.
Willmann, et al., "Small-volume frequency-domain oximetry: phantom experiments and first in vivo results," Journal of Biomedical Optics, 8(4): 618-628, Oct. 2003.
Wolfberg, "The Future of Fetal Monitoring," Reviews in Obstetrics & Gynecology, 5(3/4), pp. e132 thru e136, 2012.
Woo, et al., "Achieving higher-value obstetrical care," American Journal of Obstetrics & Gynecology, pp. 250-255 and 250.e1 thru 250.e8, Mar. 2017.
XP the Xperts in Power , 400-2500 Watts fleX, 400-2500 Watts fleXPower Series, Product information sheet, xppower.com, pp. 1 to 10, Jan. 5, 2016.
Yamaleyeva, et al., "Photoacoustic imaging for in vivo quantification of placental oxygenation in mice," The FASEB Journal, 31(12): 5520-5529, 2017.
Yamashiro, E., et al., "Fetal tolerance of maternal resuscitative endovascular balloon occlusion of the aorta in a sheep model," Am. J. Obstetrics & Genecology, Supplemental to Jan. 2020, pp. S718-S719, Jan. 2020.
Yan, et al., "Reduction of motion artifact in pulse oximetry by smoothed pseudo Wigner-Ville distribution," Journal of NeuroEngineering and Rehabilitation, 2(3), pp. 1-9, Mar. 1, 2005.
Yousefi, et al., "Adaptive Cancellation of Motion Artifact in Wearable Biosensors," 34th Annual International Conference of the IEEE EMBS, San Diego, California USA, Aug. 28-Sep. 1, 2012, pp. 5.
Yuan, et al., "Motion Artefact Minimisation from Photoplethysmography based Non-invasive Hemoglobin Sensor by the Envelope Method," Measurements, 115, pp. 1-18, Feb. 2018 (Draft Only).
Zhang, et al., "Adaptive filtering for global interference cancellation and real-time recovery of evoked brain activity: a Monte Carlo simulation study," Journal of Biomedical Optics, 12(4), pp. 044014-1 thru 044014-12, Jul./Aug. 2007.
Zhao, et al., "In vivo determination of the optical properties of infant brain using frequency-domain near-infrared spectroscopy," Journal of Biomedical Optics, 10(2), pp. 024028-1 thru 024028-7, Mar./Apr. 2005.
Zhao, et al., "Quantitative real-time pulse oximetry with ultrafast frequency frequency-domain diffuse optics and deep neural network processing," Biomedical Optics Express, 9(12): 5997-6008, 2018.
Zijistra, et al., "Absorption Spectra of Human Fetal and Adult Oxyhemoglobin, De-Oxyhemoglobin, Carboxyhemoglobin, and Methemoglobin," Clinical Chemistry, 37(9): 1633-1638, 1991.
Zourabian, et al., "Trans-abdominal monitoring of fetal arterial blood oxygenation using pulse oximetry," Journal of Biomedical Optics, 5(4): 391-405, Oct. 2000.
Goodlin, "Preliminary experience with intrapartum fetal pulse oximetry in humans," Obstetrics and Gynecology, 82(2): 314-315, Jul. 31, 1993.
Graham, et al., "A systematic review of the role of intrapartum hypoxia-ischemia in the causation of neonatal encephalopathy," American Journal of Obstetrics & Gynecology, pp. 587-595, Dec. 2008.
Greene, "Obstetricians Still Await a Deus ex Machina," The New England Journal of Medicine, 355: 2247-2248, Nov. 23, 2006.
Gregg, et al., "Brain specificity of diffuse optical imaging: improvements from superficial signal regression and tomography," Frontiers in NeuroEnergetics, 2(13), pp. 1-8, Jul. 14, 2010.
Grimes, et al., "Electronic Fetal Monitoring as a Public Health Screening Program: The Arithmetic of Failure," Obstetrics & Gynecology, 116(6): 1397-1400, Dec. 2010.
Gunn, et al., "Fetal Hypoxia Insults and Patterns of Brain Injury: Insights from Animal Models," Clin Perinatol, 36: 579-593, 2009.
Harini, et al., "Design and Implementation of a Calibration-Free Pulse Oximeter", In: Goh J. (eds) The 15th International Conference on Biomedical Engineering. IFMBE Proceedings, vol. 43, Springer, Cham, pp. 100-103, 2014.
Haydon, et al., "The effect of maternal oxygen administration on fetal pulse oximetry during labor in fetuses with nonreassuring fetal heart rate patterns," American Journal of Obstetrics and Gynecology, 195: 735-738, 2006.
Haykin, In Kalman Filtering and Neural Networks, Ed. Simon Haykin, John Wiley & Sons, Inc., New York, NY, pp. 298, 2001.

(56) References Cited

OTHER PUBLICATIONS

Hiraoka, et al., "A Monte Carlo investigation of optical pathlength in inhomogeneous tissue and its application to near-infrared spectroscopy," Institute of Physics and Engineering in Medicine, 38: 1859-1876, 1993.
Hyvärinen, "Fast and Robust Fixed-Point Algorithms for Independent Component Analysis," IEEE Trans. on Neural Networks, 10(3): 626-634, 1999.
International Commission on Non-Ionizing Radiation Protection (ICNIRP), "ICNIRP Guidelines on Limits of Exposure to Incoherent Visible and Infrared Radiation," Health Physics, 105(1): 74-96; 2013.
International Search Report and the Written Opinion of the International Searching Authority for International Application No. PCT/US19/40639 dated Nov. 12, 2019.
International Search Report and the Written Opinion of the International Searching Authority for International Application No. PCT/US2017/062782, dated Feb. 19, 2018.
International Search Report and Written Opinion dated Mar. 13, 2017, from the International Searching Authority, for International Patent Application No. PCT/US2016/068994 (filed Dec. 28, 2016), 13 pages.
Jacques, "Corrigendum: Optical properties of biological tissues: a review," IOP Publishing, Phys. Med. Biol. 58: 5007-5008, Jun. 27, 2013.
Jacques, "Optical properties of biological tissues: a review," IOP Publishing, Phys. Med. Biol. 58: R37-R61, May 10, 2013.
Jezewski, et al., "Extraction of Fetal Heart-Rate Signal as the Time Event Series From Evenly Sampled Data Acquired Using Doppler Ultrasound Technique," IEEE Transactions on Biomedical Engineering, 55(2): 805-810, Feb. 2008.
Johnson et al., "Continuous fetal monitoring with a pulse oximeter: a case of cord compression," Am. J. Obstet. Gynecol., 161(5): 1295-1296, Nov. 1989 (Abstract Only).
Johnson, et al., "Continuous Intrapartum Measurement of Fetal Oxygen Saturation," The Lancet, pp. 517, Aug. 27, 1988.
Johnson, et al., "Fetal monitoring with pulse oximetry," British Journal of Obstetrics and Gynaecology, 98: 36-41, Jan. 1991.
Julious, "Sample size of 12 per group rule ofthumb for a pilot study," Pharmaceut. Statist., 4: 287-291, 2005.
Jumadi, et al., Development of theoretical oxygen saturation calibration curve based on optical density ratio and optical simulation approach,: AIP Conference Proceedings 1883, pp. 1-11, Sep. 14, 2017.
Jumadi, et al., "Investigating the Effect of Total Radiated Power on Fetus Using Optical Simulation Approach Based on Exposure Safety Limit for Eye and Tissue Injury," Journal of Life Sciences and Technologies, 2(1): 24-27, Jun. 2014.
Jumadi, et al., "Transabdominal Fetal Pulse Oximeter Using LEDs and Photodiode: A Design Consideration Study," 2015 2nd International Conference on Biomedical Engineering (ICoBE), pp. 1-6, Mar. 30-31, 2015.
Jurovata, et al., "Simulation of Photon Propagation in Tissue Using Matlab", Faculty of Materials Science and Technology in Trnava Slovak University of Techology in Bratislava, Research Papers (2013), 21:31-37.
Kainerstorfer, et al., "Optical oximetry of volume-oscillating vascular compartments: contributions from oscillatory blood flow," Journal of Biomedical Optics, 21(10): pp. 101408-1-101408-13, Oct. 2016.
Kelly, et al., "Dose-dependent relationship between acidosis at birth and likelihood of death or cerebral palsy," Arch Dis Child Fetal Neonatal Ed 2017, pp. F1-F6, 2017.
Kim, et al., "Noise reduction of PPG signal during Free Movements Using Adaptive SFLC (scaled Fourier linear combiner)," IFMBE proceedings, pp. 1083-1086, Jan. 2007.
Kirschbaum, et al., "Oxyhemoglobin dissociation characteristics of human and sheep maternal and fetal blood," Am. J. Obstetric and Gynecology, 96(5): 741-759, 1966.

Klauser, et al., "Use of fetal pulse oximetry among high-risk women in labor: A randomized clinical trial," American Journal of Obstetrics and Gynecology, 192: 1810-1817, 2005.
Kohl, et al., "Determination of the wavelength dependence of the differential pathlength factor from near-infrared pulse signals," Physics in Medicine & Biology, 43: 1771-1782, 1998.
Komalla, "A new method based on complex EMD for motion artifacts reduction in PPG signals for pulse oximeter application," Journal of Engineering Technology, Special Issue on Technology Applications and Innovations, 6: 187-200, 2017.
Konugolu Venkata Sekar, "Broadband Time-Domain Disffuse Optics for Clinical Diagnostics and Diffuse Raman Spectroscopy," Doctoral Dissertation, Politecnico de Milano, Physics Department, pp. 1-288, 2016.
Kuhnert, et al., "Intrapartum management of nonreassuring fetal heart rate patterns: A randomized controlled trial of fetal pulse oximetry," American Journal of Obstetrics and Gynecology, 191: 1989-1995, 2004.
Lakowicz, et al., "Frequency-Domain Measurements of Photon Migration in Tissues," Chemical Physics Letters, 166(3): 246-252, Feb. 23, 1990.
Laqua, et al., "A phantom with pulsating artificial vessels for non-invasive fetal pulse oximetry", Conf Proc IEEE Eng Med Biol Soc., pp. 5631-5634, 2014.
Laqua, et al., "FPGA controlled artificial vascular system," Current Directions in Biomedical Engineering, 1: 446-449, 2015.
Laqua, et al., "Improved FPGA controlled artificial vascular system for plethysmographic measurements", Current Directions in Biomedical Engineering, 2(1): 689-693, 2016.
Larosa, et al., "Understanding the full Spectrum of Organ Injury Following Intrapartum Asphixia," Frontiers in Pediatrics, 5(16): 1-11, Feb. 17, 2017.
Larsen, "Pulse Oximetry Devices Market," Meddevicetracker, Pharma Intelligence, pp. 1-58, Dec. 2017.
Lear, et al., "The peripheral chemoreflex: indefatigable guardian offetal physiological adaptation to labour," The Journal of Physiology, pp. 1-13, 2018.
Lemieux, et al., "Investigating non-Gaussian scattering processes by using nth-order intensity correlation functions," 16(7): 1651-1664, Jul. 1999.
Leszczynska-Gorzelak, et al., "Intrapartum cardiotocography and fetal pulse oximetry in assessing fetal hypoxia," International Journal of Gynecology & Obstetrics, 76: 9-14, 2002.
Louie, et al., "Four Types of Pulse Oximeters Accurately Detect Hypoxia during Low Perfusion and Motion," Anesthesiology, pp. 1-11, 2017.
Luttkus, et al., "Pulse oximetry during labour—does it give rise to hope? Value of saturation monitoring in comparison to fetal blood gas status," European Journal of Obstetrics & Gynecology and Reproductive Biology, 110, pp. S132-S138, 2003.
Mallinckrodt, Inc., "(N-400) Fetal Oxygen Saturation Monitoring System," Summary of Safety and Effectivenes Information Data, p. 31, 2000.
Mannheimer, et al., "Wavelength Selection for Low-Saturation Pulse Oximetry," IEEE Transactions on Biomedical Engineering, 44(3): 148-158, Mar. 1997.
Martinek, et al., "Non-Invasive Fetal Monitoring: A Maternal Surface ECG Electrode Placement-Based Novel Approach for Optimization of Adaptive Filter Control Parameters Using the LMS and RLS Algorithms," Sensors, 17: 1154, pp. 1-32, May 19, 2017.
Martinello, et al., "Management and investigation of neonatal-encephalopathy: 2017 update," Arch Dis Child Fetal Neonatal , 102: pp. F346-F-358, 2017.
"Anesthesia for Fetal Procedures and Surgery," pp. 280-281.
"Assessing the Photobiological Safety of LEDs," pp. 1-8, 2012.
"Corometrics™ 250 Series Monitor Operator's Manual", GE Healthcare, Revision E (Apr. 28, 2009), 258 pgs.
"Fetal Pulse Oximetry System Clinical Use Guide", OxiFirst, Nellcor (2003), 60 pgs.
"Narrow beam LED in Dragon Dome package (850nm)", OSRAM Opto Semiconductors (Mar. 10, 2014), Version 1.3, SFH 4783, pp. 1-12.

(56) References Cited

OTHER PUBLICATIONS

"OSRAM Opto Semiconductors GF CSHPM1.24-3S4S-1", Mouser Electronics (accessed Dec. 2016), 2 pgs.

Aaronson, et al., "Android-Based Tocodynamometer and Fetal Heart Rate Monitor," Tocotronics (2013), 21 pgs.

Ahearne, et al., "Short and long term prognosis in perinatal asphyxia: An update," World Journal of Clinical Pediatrics, 5(1): 67-74, Feb. 8, 2016.

Aldrich, et al., "Late fetal heart decelerations and changes in cerebral oxygenation during the first stage of labour," British Journal of Obstetrics and Gynaecology, 102: 9-13, Jan. 1995.

Alfirevic, et al., "Continuous cardiotocography (CTG) as a form of electronicfetal monitoring (EFM) for fetal assessment during labour (Review)," Cochrane Database of Systematic Reviews 2017, Issue 2. Art. No. CD006066, pp. 1 to 56, 2017.

Amer, et al., "Xenon Combined With Hypothermia in Perinatal Hypoxic-Ischemic Encephalopathy: A Noble Gas, a Noble Mission," Pediatric Neurology, 84: 5-10, Jul. 2018.

Angelo, et al., "Review of structured light in diffuse optical imaging," Journal of Biomedical Optics 24(7), 071602 (Jul. 2019), 20 pages.

Arridge, "Inverse Problems in Optical Tomography," INI Cambridge, pp. 1-74, Aug. 24, 2011.

Arridge, "Optical tomography in medical imaging," Inverse Problems, 15: R41-R93, 1999.

Arridge, et al., "The theoretical basis for the determination of optical path lengths in tissue: temporal and frequency analysis," Physics in Medicine & Biology, 37(7): 1531-1560, 1992.

Ayres-De-Campos, "Electronic fetal monitoring orcardiotocography, 50 years later: what's in a name?," American Journal of Obstetrics & Gynecology, 218(6): 545-546, Jun. 2018.

Bansal, et al., "Wearable Organic Optoelectronic Sensors for Medicine," Advanced Materials (2014), 7 pgs.

Barry, et al., "The Pregnant Sheep as a Model for Human Pregnancy," Theriogenology, 69(1): 55-67, Jan. 1, 2008.

Bauer, et al., "Quantitative photoacoustic imaging:correcting for heterogeneous light fluence distributions using diffuse optical tomography," Journal of Biomedical Optics, 16(9): 096016-1-096016-7, Sep. 2011.

Belfort, et al., "A Randomized Trial of Intrapartum Fetal ECG ST-Segment Analysis," The New England Journal of Medicine, 373(7): 632-641, Aug. 13, 2015.

Bennet, et al., "The Cerebral Hemodynamic Response to Asphyxia and Hypoxia in the Near-term Fetal Sheep as Measured by Near Infrared Spectroscopy," Pediatric Research, 44: 951-957, Dec. 1, 1998.

Bennet, et al., "The Fetal Heart RateResponse to Hypoxia: Insights from Animal Models," Clin Perinatol, 36: 655-672, 2009.

Bevilacqua, et al., "In vivo local determination of tissue optical properties: applications to human brain," Applied Optics, 38(22): 4939-4950, 1999.

Bloom, et al., "Fetal Pulse Oximetry and Cesarean Delivery," The New England Journal of Medicine, 355: 2195-2202, Nov. 23, 2006.

Bloom, et al., "Fetal Pulse Oximetry: Duration of Desaturation and Intrapartum Outcome," Journal of Obstetrics and Gynecology, 93(6): 1036-1040, Jun. 1999.

Bloom, et al., "What We Have Learned About Intrapartum Fetal Monitoring Trials in the MFMU Network," Author Manuscript, Semin Perinatol, 40(5): 307-317, Aug. 2016.

Boas, et al., "Diffuse optical imaging of brain activation: approaches to optimizing image sensitivity, resolution, and accuracy," NeuroImage, 23: S275-S288, 2004.

Boas, et al., "Scattering and Imaging with Diffusing Temporal Fields Correlation," Physical Review Letters, 75(9): 1855-1859, Aug. 28, 1995.

Boas, et al., "Spatially varying dynamical properties of turbidmedia probed withdiffusing temporal light correlation," J. Opt. Soc. Am., 14(1): 192-215, Jan. 1997.

Bottrich, et al., "Signal Separation for Transabdominal Non-invasive Fetal Pulse Oximetry using Comb Filters," ConfProc IEEE Eng Med Biol Soc, pp. 5870-5873, 2018.

Bozkurt, et al., "Safety assessment of near infrared light emitting diodes for diffuse optical measurements," BioMedical Engineering Online, 3(1): pp. 10, Mar. 22, 2004.

Buckley, et al., "Diffuse correlation spectroscopy formeasurement of cerebral blood flow: future prospects," Neurophotonics, 1(1), pp. 011009-1-011009-7, Jul.-Sep. 2014.

Buschmann, et al., "Fetal oxygen saturation measurement by transmission pulse oximetry," The Lancet, 339: 615, Mar. 7, 1992.

Cahill, et al., "A prospective cohort study of fetal heart rate monitoring: deceleration area is predictive of feal acidemia," American Journal of Obstetrics & Gynecology, 218(5), pp. 523.e1-523. e12, May 2018.

Caliskan, et al., "Reduction in caesarean delivery with fetal heartrate monitoring and intermittent pulse oximetryafter induction of labour with misoprostol," The Journal of Maternal-Fetal & Neonatal Medicine, 22(5): 445-451, May 2009.

Carbonne, et al., "Fetal pulse oximetry: correlation between changes in oxygen saturation and neonatal outcome. Preliminary report on 39 cases," European Journal of Obstetrics & Gynecology and Reproductive Biology, 57: 73-77, 1994.

Carbonne, et al., "Multicenter oximetry study on the clinical value of fetal pulse oximetry," Am J Obstet Gynecol, 177(3): 593-598, 1997.

Carter, et al., "Calibration of a Reflectance Pulse Oximeter in Fetal Lambs for Arterial Oxygen Saturations Below 70%," J Soc Gynecol Invest, 5(5): 255-259, Sep.-Oct. 1998.

Cerebral Palsy Guidance, Cerebral Palsy, Cerebral Palsy Guidance Website, pp. 1 to 14, 2018.

Chan, et al., "Effects of Compression on Soft Tissue Optical Properties," IEEE Journal of Selected Topics in Quantum Electronics, 2(4): 943-950, Dec. 1996.

Chandraharan, "Fetal scalp blood sampling during labour: is it auseful diagnostic test or a historical test that nolonger has a place in modern clinical obstetrics?" Royal College of Obstetricians and Gynaecologists, www.bjog.org, pp. 1056-1062, Mar. 6, 2014.

Cheung, et al., "In vivo cerebrovascular measurement combining diffuse near-infrared absorption and correlation spectroscopies," Physics in Medicine & Biology, 46: 2053-2065, 2001.

Choe, "Diffuse Optical Tomography and Spectroscopy of Breast Cancer and Fetal Brain," Pub'd, Sep. 29, 2005, A Dissertation in Physics and Astronomy, Faculties of the University of Pennsylvania.

Choe, et al., "Transabdominal near infrared oximetry of hypoxic stress in fetal sheep brain in utero," PNAS, 100(22): 12950-12954, Oct. 28, 2003.

Clark, et al., "Intrapartum management of category II fetal heart rate tracings: towards standardization of care," American Journal of Obstetrics & Gynecology, pp. 89-97, Aug. 2013.

Clark, et al., "The limits of electronic fetal heart rate monitoring in the prevention of neonatal metabolic acidemia," American Journal of Obstetrics & Gynecology, 216, pp. 163.e1-163.e6, Feb. 2017.

Colditz, et al., "Fetal pulse oximetry: Instrumentation and Recent Clinical Experience," Clinics in Perinatology, 26(4): 869-880, Dec. 1999.

Dassel, et al., "Reflectance Pulse Oximetry in Fetal Lambs," Pediatric Research, 31(3): 266-269, 1992.

De Blasi, et al., "Noninvasive measurement of human forearm oxygen consumption by near infrared spectroscopy," European Journal of Applied Physiology, 67: 20-25, 1993.

Delpy, et al., "Estimation of optical pathlength through tissue from direct time of flight measurement," Physics in Medicine & Biology, 33(12): 1433-1442, 1988.

SYSTEMS, DEVICES, AND METHODS FOR PERFORMING TRANS-ABDOMINAL FETAL OXIMETRY AND/OR TRANS-ABDOMINAL FETAL PULSE OXIMETRY USING INDEPENDENT COMPONENT ANALYSIS

RELATED APPLICATION

This application is a Continuation of U.S. application Ser. No. 16/958,136 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING INDEPENDENT COMPONENT ANALYSIS" filed 25 Jun. 2020, which is a U.S. National Phase Application of PCT/US2018/068042 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING INDEPENDENT COMPONENT ANALYSIS" filed 28 Dec. 2018, which is a non-provisional of, and claims priority to, U.S. Provisional Patent Application No. 62/611,849 entitled "SYSTEMS, DEVICES, AND METHODS FOR PERFORMING TRANS-ABDOMINAL FETAL OXIMETRY AND/OR TRANS-ABDOMINAL FETAL PULSE OXIMETRY USING INDEPENDENT COMPONENT ANALYSIS" filed 29 Dec. 2017, all of which are incorporated by reference, in their entireties, herein.

FIELD OF INVENTION

The present invention is in the field of medical devices and, more particularly, in the field of trans-abdominal fetal oximetry and trans-abdominal fetal pulse oximetry.

BACKGROUND

Oximetry is a method for determining the oxygen saturation of hemoglobin in a mammal's blood. Typically, 90% (or higher) of an adult human's hemoglobin is saturated with (i.e., bonded to) oxygen while only 30-60% of a fetus's blood is saturated with oxygen. Pulse oximetry is a type of oximetry that uses changes in blood volume through a heartbeat cycle to internally calibrate hemoglobin oxygen saturation measurements of the arterial blood.

Current methods of monitoring fetal health, such as monitoring fetal heart rate, are inefficient at determining levels of fetal distress and, at times, provide false positive results indicating fetal distress that may result in the unnecessary performance of a Cesarean section.

SUMMARY

Systems, devices, and methods for performing trans-abdominal fetal oximetry and/or trans-abdominal fetal pulse oximetry using independent component analysis are herein described. In one embodiment, a plurality of detected electronic signals may be received. Each of the plurality of detected electronic signals may be received from a separate detector (e.g., a photodetector) communicatively coupled to the processor and may correspond to a detected optical signal emanating from a pregnant mammal's abdomen and a fetus contained therein. Each detected optical signal may be converted, by the respective detector, into one of the plurality of the detected electronic signals. The detected optical signals may correspond to light that is projected into the pregnant mammal's abdomen from a light source. The light may include two or more different wavelengths, or ranges of wavelengths, of light. For example, the light projected into the pregnant mammal's abdomen may be within the range of red, near infrared, and/or infrared light.

Independent component analysis may then be performed on the plurality of detected electronic signals to separate signals within the detected electronic signals that are contributed by different sources (e.g., maternal photoplethysmogram, a fetal photoplethysmogram, a maternal respiratory signal, a uterine tone signal, and/or a noise signal). Each of the separated signals may correspond to a different source.

The separated signals may be analyzed to determine a separated signal that corresponds to light incident upon the fetus. In some embodiments, the separated signal that corresponds to light incident upon the fetus is a fetal photoplethysmogram signal. The separated signal that corresponds to light incident upon the fetus may be analyzed to determine a fetal hemoglobin oxygen saturation level of the fetus. An indication of the fetal hemoglobin oxygen saturation level may then be provided to the user. At times, the fetal oxygen saturation level may be provided to the user as a numerical value or as a value depicted on a graph. In some instances, the fetal hemoglobin oxygen saturation level may be provided as a time weighted average taken over, for example, 30 seconds, 1, 2, 5, 10, 20, and/or 30 minutes.

In some embodiments, a separated signal that corresponds to light incident upon the pregnant mammal (e.g., maternal photoplethysmogram, a maternal respiratory signal, a uterine tone signal, etc.) may be analyzed to determine, for example, a condition of the pregnant mammal and/or how the separated signal that corresponds to light incident upon the pregnant mammal contributes to the initially received detected electronic signals. Then, an indication of the analysis results may be provided to the user.

In some embodiments, the received plurality of detected electronic signals may be filtered and/or amplified prior to performance of the independent component analysis. At times, this filtering and/or amplification may incorporate use of a received secondary signal (e.g., maternal heart rate, fetal heart rate, noise, etc.). When a secondary signal is received, it may be synchronized in time and/or phase with the secondary signal prior to filtering the received plurality of detected electronic signals.

In another embodiment, a processor may receive a first detected electronic signal from a first detector, a second detected electronic signal from a second detector, and a third detected electronic signal from a third detector. Each of the first, second, and third detectors may be communicatively coupled to the processor. Each of the first, second, and third detected electronic signals may correspond to a detected optical signal emanating from a pregnant mammal's abdomen and a fetus contained that is detected by the respective first, second, and third detectors and converted into the respective first, second, and third detected electronic signals. The detected optical signal may correspond to an optical signal projected into the pregnant mammal's abdomen by one or more light sources.

The processer may perform independent component analysis on the first, second, and third detected electronic signals to generate a first separated signal, a second separated signal, and a third separated signal. The first separated signal, second separated signal, and third separated signal may be contributed to the first, second, and third detected electronic signals by a first source, a second source, and a third source, respectively. One of the separated signals (e.g., the third separated signal) may correspond to a fetal photoplethysmogram signal. The separated signal that corresponds to the fetal photoplethysmogram signal may then be analyzed to determine a hemoglobin oxygen saturation level of the fetus. Provision of an indication of the hemoglobin oxygen saturation level of the fetus to a user may then be facilitated.

In some embodiments, the first source of the first separated signal may be motion artifacts of the pregnant mammal, respiration of the pregnant mammal, photoplethysmogram variations of the pregnant mammal, uterine tone of the pregnant mammal, or noise.

In some embodiments, the second source of the second separated signal may be motion artifacts of the pregnant mammal, respiration of the pregnant mammal, photoplethysmogram variations of the pregnant mammal, uterine tone of the pregnant mammal, and noise. In most cases, the source of the second source will not be the same as the first source.

At times, a fourth detected electronic signal from a fourth detector may be received by the processor prior to performance of the independent component analysis. The fourth detected electronic signal may correspond to a detected optical signal emanating from the pregnant mammal's abdomen and contained fetus that is detected by the fourth detector and converted into the fourth detected electronic signal. The independent component analysis may be performed on/using the first, second, third, and fourth detected electronic signals to generate the first separated signal, the second separated signal, the third separated signal, and a fourth separated signal. The fourth separated signal may be contributed by a fourth source. Exemplary fourth sources include, but are not limited to, motion artifacts of the pregnant mammal, respiration of the pregnant mammal, photoplethysmogram variations of the pregnant mammal, uterine tone of the pregnant mammal, and noise.

BRIEF DESCRIPTION OF THE FIGURES

The present invention is illustrated by way of example, and not limitation, in the figures of the accompanying drawings in which.

DESCRIPTION

Described herein are systems, devices, and methods for performing transabdominal fetal oximetry and/or fetal pulse oximetry. A key output of fetal oximetry and/or fetal pulse oximetry is the level of oxygen saturation of the fetus's blood (also referred to herein as "fetal hemoglobin oxygen saturation level" and "oxygen saturation level") which may also be understood as the percentage of hemoglobin present in the fetus' blood that is bound to oxygen. The oxygen saturation level of a fetus' blood may be used by trained medical professionals to assess the health of a fetus (e.g., a level of hypoxia or fetal acidosis) as well as a level of stress it may be under during, for example, a labor and delivery process. Typically, values of oxygen saturation for fetal blood fall within the range of 30-60% with anything lower than 30% indicating that the fetus may be in distress.

For the purposes of the following discussion, the terms "pregnant mammal" or "maternal" or "mother" is used to refer to a female human being or animal (e.g., horse or cow) pregnant with a fetus. In most embodiments, the pregnant individual will be a human being, but this need not be the case as the invention may be used for nearly any pregnant mammal.

Figure 1:
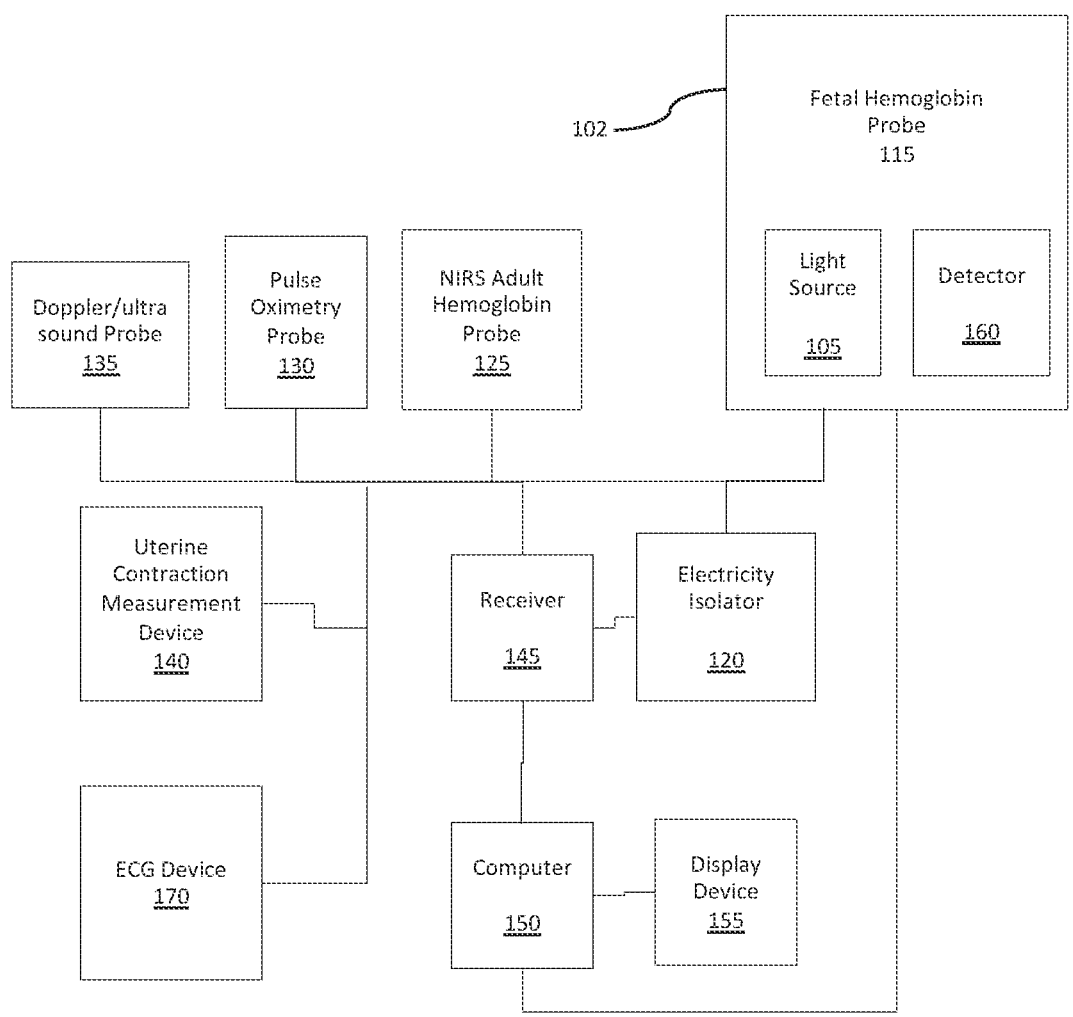
FIG. 1 is a block diagram illustrating an exemplary system for determining a fetal hemoglobin oxygen saturation level, consistent with some embodiments of the present invention.

FIG. 1 is a block diagram illustrating an exemplary system 100 for performing fetal oximetry and/or fetal pulse oximetry trans-abdominally and/or in-utero to determine fetal hemoglobin oxygen saturation level using independent component analysis. The components of system 100 may be coupled together via wired and/or wireless communication links. In some instances, wireless communication of one or more components of system 100 may be enabled using short-range wireless communication protocols designed to communicate over relatively short distances (e.g., BLUETOOTH®, near field communication (NFC), radio-frequency identification (RFID), and Wi-Fi) with, for example, a computer or personal electronic device (e.g., tablet computer or smart phone) as described below. Electrical power may be supplied to system 100 and/or any component thereof via, for example, an on-board power supply (e.g., battery) and/or a coupling (e.g., plug) to an external power supply (e.g., electrical main). In some instances, a battery may be rechargeable.

System 100 includes a light source 105 and a detector 160 that, at times, may be housed in a single housing, which may be referred to as fetal hemoglobin probe 115. In some instances, fetal hemoglobin probe 115 may be a pulse oximetry device or pulse oximeter. Light source 105 may include a single, or multiple light sources and detector 160 may include a single, or multiple detectors.

Light source(s) 105 may transmit light at light of one or more wavelengths, including light within the red, near infra-red (NIR), and/or infrared bands of the electromagnetic spectrum into the pregnant mammal's abdomen. Typically, the light emitted by light source(s) 105 will be focused or emitted as a narrow beam to reduce spreading of the light upon entry into the pregnant mammal's abdomen.

Light source(s) 105 may be, for example, a LED, and/or a LASER, a tunable light bulb and/or a tunable LED that may, in some instances, be coupled to a fiber optic cable. In some instances, the light source(s) 105 may be tunable or otherwise user configurable while, in other instances, one or more of the light sources may be configured to emit light within a pre-defined range of wavelengths. Additionally, or alternatively, one or more filters (not shown) and/or polarizers may filter/polarize the light emitted by light source(s) 105 to be of one or more preferred wavelengths. These filters/polarizers may also be tunable or user configurable.

In some embodiments, light source(s) 105 may be an array of two or more light source(s) 105. An exemplary light source 105 is one with a relatively small form factor and high efficiency so as to limit heat emitted by the light source 105. In one embodiment, light source 105 is configured to emit light at 850 nm an example of which is the LED in Dragon Dome Package that Emits Light of 850 nm manufactured by OSRAM Opto Semiconductors (model number SFH 4783), which has a length of 7.080 mm and a width of 6.080 mm.

In some embodiments, one or more light sources 105 may be a fiber optic cable transmitting light produced by another source (e.g., a LASER or tunable light bulb or LED) not resident within fetal hemoglobin probe 115. In some instances, the light source(s) 105 may be tunable or otherwise user configurable while, in other instances, one or more of the light sources may be configured to emit light within a pre-defined range of wavelengths. Additionally, or alternatively, one or more filters (not shown) and/or polarizers may filter/polarize the light emitted by light source(s) 105 to be of one or more preferred wavelengths. These filters/polarizers may also be tunable or user configurable.

An exemplary light source 105 may have a relatively small form factor and may operate with high efficiency, which may serve to, for example, conserve space and/or limit heat emitted by the light source 105. In one embodiment, light source 105 is configured to emit light in the range of 770-850 nm. Exemplary flux ratios for light source(s) include but are not limited to a luminous flux/radiant flux of 175-260 mW, a total radiant flux of 300-550 mW and a power rating of 0.6 W-3.5 W.

Detector 160 may be configured to detect a light signal emitted from the pregnant mammal and/or the fetus via, for example, transmission and/or back scattering. Detector 160 may convert this light signal into an electronic signal, which may be communicated to a computer or processor and/or an on-board transceiver that may be capable of communicating the signal to the computer/processor. The optical light detected and converted into an electrical signal by detector 160 may be referred to herein as a detected electronic signal. This detected electronic signal might then be processed in order to determine how much light, at various wavelengths, is incident upon, scattered by, and/or absorbed by the fetal oxyhemoglobin and/or de-oxyhemoglobin so that a fetal hemoglobin oxygen saturation level may be determined. This processing will be discussed in greater detail below.

Exemplary detectors 160 include, but are not limited to, cameras, traditional photomultiplier tubes (PMTs), silicon PMTs, avalanche photodiodes, and silicon photodiodes. In some embodiments, the detectors may have a relatively low cost (e.g., $50 or below), a low voltage requirement (e.g., less than 100 volts), and non-glass (e.g., plastic) form factor. However, these alternatives do not have the same sensitivity as PMTs. In other embodiments, (e.g., contactless pulse oximetry) a sensitive camera may be deployed to receive light exiting the pregnant mammal's abdomen. For example, detector 160 may be a sensitive camera adapted to capture small changes in fetal skin tone caused by changes in cardiovascular pressure as the fetus' heart beats. In these embodiments, detector 160 and/or fetal hemoglobin probe 115 may be in contact with the pregnant mammal's abdomen, or not, as this embodiment may be used to perform so-called contactless pulse oximetry. In these embodiments, light source(s) 105 may be adapted to provide light (e.g., in the visible spectrum, near-infrared, etc.) directed toward the pregnant mammal's abdomen so that the detector 160 is able to receive/detect light exiting the pregnant mammal's abdomen and fetus. The light captured by detector 160 may be communicated to computer 150 for processing to convert the images to a measurement of fetal hemoglobin oxygen saturation according to, for example, one or more of the processes described herein.

A fetal hemoglobin probe 115, light source 105, and/or detector 160 may be of any appropriate size and, in some circumstances, may be sized to accommodate the size of the pregnant mammal and/or fetus using any appropriate sizing system (e.g., abdomen size and/or fetus age, etc.). Exemplary lengths for a fetal hemoglobin probe 115 include a length of 4 cm-40 cm and a width of 2 cm-10 cm. In some circumstances, the size and/or configuration of a fetal hemoglobin probe 115, or components thereof, may be responsive to skin pigmentation of the pregnant mammal and/or fetus. In some instances, the fetal hemoglobin probe 115 may be applied to the pregnant mammal's skin via tape or a strap that cooperates with a mechanism (e.g., snap, loop, etc.) (not shown).

System 100 includes a number of optional independent sensors/probes designed to monitor various aspects of maternal and/or fetal health and may be in contact with a pregnant mammal. These probes/sensors are a NIRS adult hemoglobin probe 125, a pulse oximetry probe 130, a Doppler and/or ultrasound probe 135, a uterine contraction measurement device 140, and an electrocardiography (ECG) device 170. Not all embodiments of system 100 will include all of these components. ECG device 170 may be used to determine the pregnant mammal's and/or fetus' heart rate. In some embodiments, system 100 may further include an intrauterine pulse oximetry probe (not shown) that may be used to determine the fetus' heart rate. The Doppler and/or ultrasound probe 135 may be configured to be placed on the abdomen of the pregnant mammal and may be of a size and shape that approximates a silver U.S. dollar coin and may provide information regarding fetal position, orientation, and/or heart rate. Pulse oximetry probe 130 may be a conventional pulse oximetry probe placed on pregnant mammal's hand and/or finger to measure the pregnant mammal's hemoglobin oxygen saturation. NIRS adult hemoglobin probe 125 may be placed on, for example, the pregnant mammal's 2nd finger and may be configured to, for example, use near infrared spectroscopy to calculate the ratio of adult oxyhemoglobin to adult de-oxyhemoglobin. NIRS adult hemoglobin probe 125 may also be used to determine the pregnant mammal's heart rate.

Optionally, system 100 may include a uterine contraction measurement device 140 configured to measure the strength and/or timing of the pregnant mammal's uterine contractions. In some embodiments, uterine contractions will be measured by uterine contraction measurement device 140 as a function of pressure (measured in e.g., mmHg) over time. In some instances, the uterine contraction measurement device 140 is and/or includes a tocotransducer, which is an instrument that includes a pressure-sensing area that detects changes in the abdominal contour to measure uterine activity and, in this way, monitors frequency and duration of contractions.

In another embodiment, uterine contraction measurement device 140 may be configured to pass an electrical current through the pregnant mammal and measure changes in the electrical current as the uterus contracts. Additionally, or alternatively, uterine contractions may also be measured via near infrared spectroscopy using, for example, light received/detected by detector 160 because uterine contractions, which are muscle contractions, are oscillations of the uterine muscle between a contracted state and a relaxed state. Oxygen consumption of the uterine muscle during both of these stages is different and these differences may be detectable using NIRS.

Measurements and/or signals from NIRS adult hemoglobin probe 125, pulse oximetry probe 130, Doppler and/or ultrasound probe 135, and/or uterine contraction measurement device 140 may be communicated to receiver 145 for communication to computer 150 and display on display device 155 and, in some instances, may be considered secondary signals. As will be discussed below, measurements provided by NIRS adult hemoglobin probe 125, pulse oximetry probe 130, a Doppler and/or ultrasound probe 135, uterine contraction measurement device 140 may be used in conjunction with fetal hemoglobin probe 115 to isolate a fetal pulse signal and/or fetal heart rate from a maternal pulse signal and/or maternal heart rate. Receiver 145 may be configured to receive signals and/or data from one or more components of system 100 including, but not limited to, fetal hemoglobin probe 115, NIRS adult hemoglobin probe 125, pulse oximetry probe 130, Doppler and/or ultrasound probe 135, uterine contraction measurement device 140, and/or ECG device 170. Communication of receiver 145 with other components of system may be made using wired or wireless communication In some instances, one or more of NIRS adult hemoglobin probe 125, pulse oximetry probe 130, a Doppler and/or ultrasound probe 135, uterine contraction measurement device 140, and/or ECG device 170 may include a dedicated display that provides the measurements to, for example, a user or medical treatment provider. It is important to note that not all of these probes may be used in every instance. For example, when the pregnant mammal is using fetal hemoglobin probe 115 in a setting outside of a hospital or treatment facility (e.g., at home or work) then, some of the probes (e.g., NIRS adult hemoglobin probe 125, pulse oximetry probe 130, a Doppler and/or ultrasound probe 135, uterine contraction measurement device 140) of system 100 may not be used.

In some instances, receiver 145 may be configured to process or pre-process received signals to, for example, make the signals compatible with computer 150 (e.g., convert an optical signal to an electrical signal), improve SNR, amplify a received signal, etc. In some instances, receiver 145 may be resident within and/or a component of computer 150. Also, receiver 145 is not limited to single receiver, as any number of appropriate receivers (e.g., 2, 3, 4, 5) may be used to receive signals from system 100 components and communicate them to computer 150. In some embodiments, computer 150 may amplify or otherwise condition the received reflected signal so as to, for example, improve the signal-to-noise ratio Receiver 145 may communicate received, pre-processed, and/or processed signals to computer 150. Computer 150 may act to process the received signals, as discussed in greater detail below, and facilitate provision of the results to a display device 155. Exemplary computers 150 include desktop and laptop computers, servers, tablet computers, personal electronic devices, mobile devices (e.g., smart phones), and the like. Exemplary display devices 155 are computer monitors, tablet computer devices, and displays provided by one or more of the components of system 100. In some instances, display device 155 may be resident in receiver 145 and/or computer 150.

In some embodiments, a pregnant mammal may be electrically insulated from one or more components of system 100 by, for example, an electricity isolator 120. Exemplary electricity isolators 120 include transformers and non-conducting materials.

Fetal hemoglobin probe 115 may be used to direct NIR light into the abdomen of the pregnant mammal so as to reach the fetus and to detect light incident upon the fetus. The NIR light may be emitted by fetal hemoglobin probe 115 in, for example, a continuous and/or pulsed manner. This reflected light might then be processed in order to determine how much light, at various wavelengths, is reflected and/or absorbed by the fetal oxyhemoglobin and/or de-oxyhemoglobin so that a fetal hemoglobin oxygen saturation level may be determined. This processing will be discussed in greater detail below. In some embodiments, fetal hemoglobin probe 115 may be configured, partially or wholly, as a single-use, or disposable, probe that is affixed to the pregnant mammal's skin on, for example, the pregnant mammal's abdomen and, in some embodiments, in the supra-pubic (bikini) region.

Exemplary dimensions for fetal hemoglobin probe 115 include, but are not limited to, 2-16 inches in length and 0.5-8 inches in width. In some instances, fetal hemoglobin probe 115 may come in a variety of sizes so as to, for example, accommodate varying clinical needs, the size of the fetus, fetal position, the size of the pregnant mammal, and/or the size of the pregnant mammal's abdomen.

The fetal hemoglobin probe(s) 115 disclosed herein may include a housing 102 configured to house one or more components of fetal hemoglobin probe 115. Although the embodiments disclosed herein have all of the components of fetal hemoglobin probes 115 contained within a single housing 102, this is not necessarily the case as, for example, two or more components of a fetal hemoglobin probe 115 may be housed in separate housings 102. Housings 102 may be, for example, square, circular, or rectangular in shape and may be designed to be, in some instances, adjustable depending on, for example, a topology of the pregnant mammal's abdomen, a level of skin pigmentation for the pregnant mammal and/or her fetus, and so on.

In some embodiments, fetal hemoglobin probe 115 and/or housing 102 may be disposable and in other embodiments, fetal hemoglobin probe 115 (including and/or housing 102) may be configured for multiple uses (i.e., reusable). In some embodiments, (e.g., when fetal hemoglobin probe is configured to be disposable), may include an adhesive designed to be applied to the skin of the pregnant mammal's abdomen (e.g., glue, tape, etc.) configured to apply housing 102/fetal hemoglobin probe 115 directly to the skin of the pregnant mammal's abdomen and hold it in place there in a manner similar to a sticker. In some instances, the fetal hemoglobin probe 115 may be applied to the pregnant mammal's skin via tape or a strap that cooperates with a mechanism (e.g., snap, loop, etc.) (not shown) provided by the housing 102. In some circumstances, housing 102 may be attached/adjacent to the pregnant mammal's skin so that it does not move, and, in other instances, it may be allowed to move in order to, for example, attain better measurements/readings. In some cases, housing 102 and/or a portion thereof may not be adapted to be in contact with the pregnant mammal's abdomen.

In some embodiments, housing 102 and/or a portion thereof may cooperate with a reusable and/or disposable sleeve (not shown) that fits over fetal hemoglobin probe 115 so that fetal hemoglobin probe 115 may be placed within a housing 102 reusable and/or disposable sleeve so that it may be applied to the pregnant mammal's skin.

Fetal hemoglobin probe 115 may be adapted to direct, or shine, light of one or more wavelengths into the abdomen of a pregnant mammal and receive a signal corresponding to a reflection of a portion of that light from the pregnant mammal's tissue and fluid as well as the tissue and fluids of the fetus.

Optionally, fetal hemoglobin probe 115 may include one or more mechanisms that enable the emitted light to be directed in a particular direction. Such mechanisms include, but are not limited to, wedges or adhesive material, that may be transparent or substantially transparent. For example, a fetal hemoglobin probe 115 may include a wedge positioned on one side that operates to direct the light in a particular direction relative to the surface of the pregnant mammal's skin and/or position a detector or transceiver to receive an optimized amount of reflected light.

In some embodiments, a fetal hemoglobin probe 115 may be adapted to be worn by a pregnant mammal for an extended period of time (e.g., days, weeks, etc.) that is not necessarily coincident with the labor and delivery process in order to, for example, monitor the health of a fetus. In some embodiments, one or more components of fetal hemoglobin probe 115 may be positioned outside the fetal hemoglobin probe 115 and may be optically connected thereto via, for example, one or more fiber optic or Ethernet cable(s).

A fetal hemoglobin probe 115 may be of any appropriate size and, in some circumstances, may be sized so as to accommodate the size of the pregnant mammal using any appropriate sizing system (e.g., waist size and/or small, medium, large, etc.). Exemplary lengths for a fetal hemoglobin probe 115 include a length of 4 cm-40 cm and a width of 2 cm-10 cm. In some circumstances, the size and/or configuration of a fetal hemoglobin probe 115, or components thereof, may be responsive to skin pigmentation of the pregnant mammal and/or fetus.

It will be understood that although the components of fetal hemoglobin probe 115 are described herein as being included in a single probe, that is not necessarily so as the components of fetal hemoglobin probe 115 may be present in two or more different objects/devices applied to a pregnant mammal. In some instances, more than one fetal hemoglobin probe 115 may be used so as to, for example, improve accuracy of the fetal oxygen saturation measurement. For example, a first fetal hemoglobin probe 115 (or a component thereof) may be placed on a left side of a pregnant mammal's abdomen and a second fetal hemoglobin probe 115 (or a component thereof) may be placed on a right side of the pregnant mammal's abdomen.

The trans-abdominal fetal oximetry processes disclosed herein may be executed, at least in part, with a fetal hemoglobin probe that includes a plurality of detectors. In general, light may be directed into the abdomen of a pregnant mammal by one or more light sources fetal hemoglobin probe resident within a housing. Some of this light may be reflected by the pregnant mammal and/or the fetus and may then be received by one of a plurality of detectors resident within the fetal hemoglobin probe housing. Power may be supplied to a fetal hemoglobin probe via, for example, a battery or an external power supply.

Figure 2A:
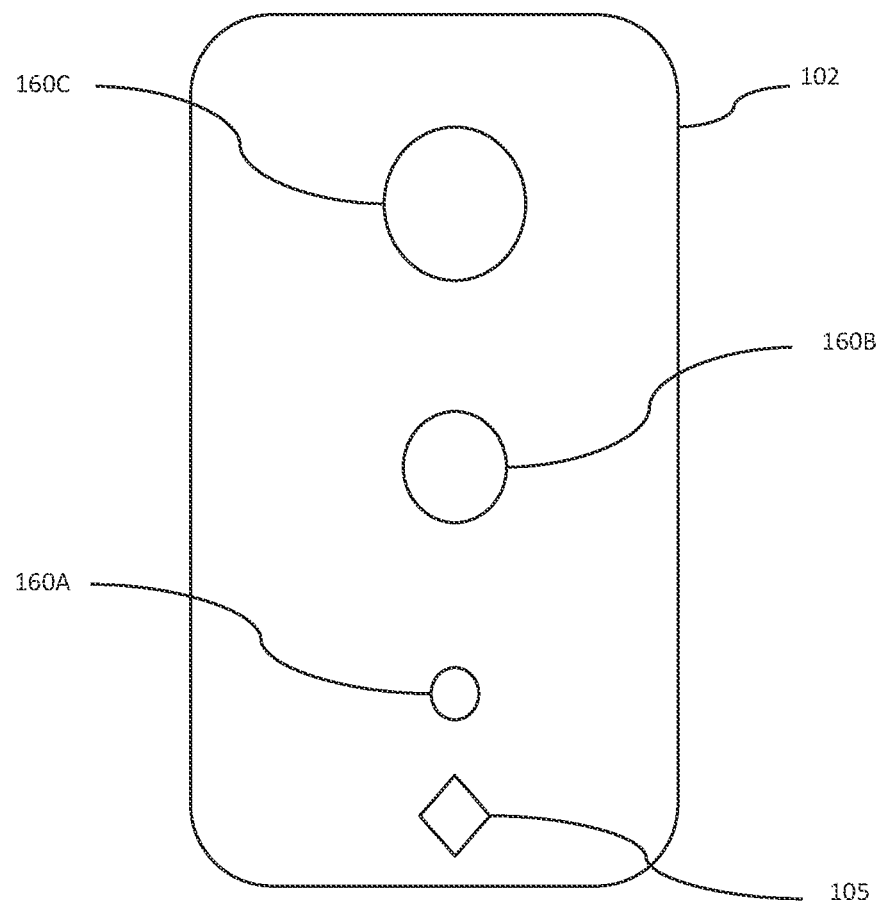
FIG. 2A provides an illustration of an exemplary fetal hemoglobin probe with three detectors, consistent with some embodiments of the present invention.
Figure 2B:
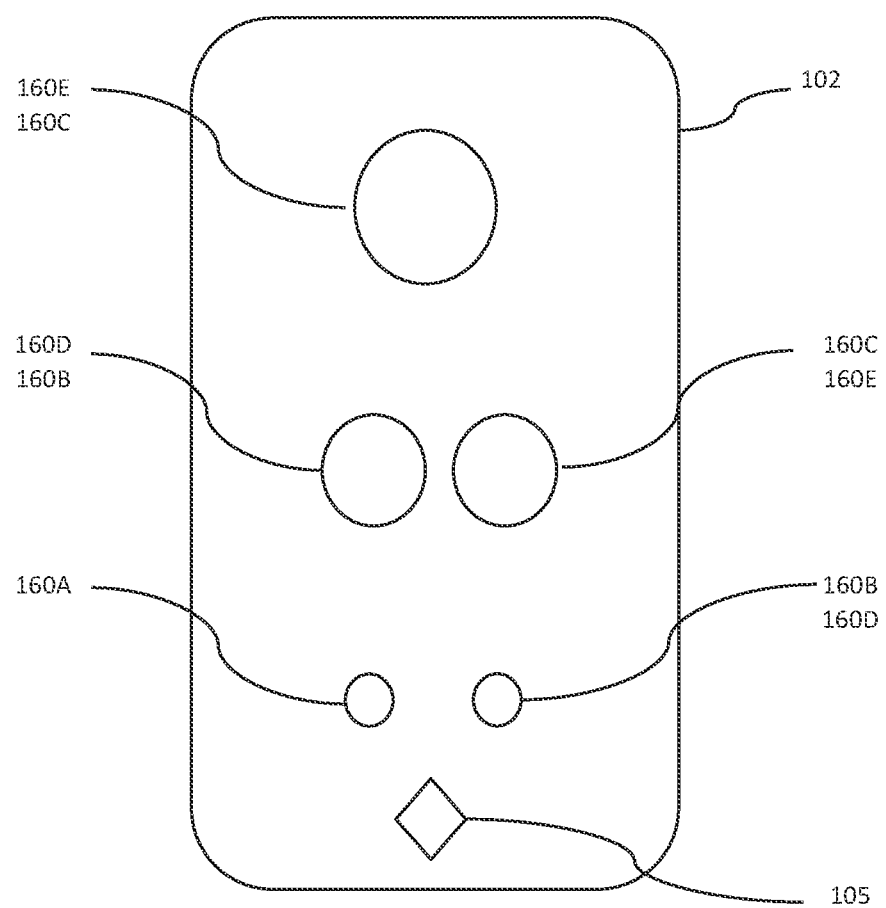
FIG. 2B provides an illustration of an exemplary fetal hemoglobin probe with five detectors, consistent with some embodiments of the present invention.

Example of a fetal hemoglobin probe are provided by FIGS. 2A and 2B, which provide an illustration of an exemplary fetal hemoglobin probes 115A and 115B, respectively. Fetal hemoglobin probe 115A includes one light source 105, a first detector 160A, a second detector 160B, and a third detector 160C positioned within a housing 102. In fetal hemoglobin probe 115A, first detector 160A is positioned closest (e.g., 0.5-3 cm) to light source 105, third detector 160C is positioned furthest away (e.g., 3-10 cm) from light source 105, and second detector 160B is positioned between first and third detectors 105A and 105C, respectively. Exemplary distances between light source 105 and detector 160B are 0.5-8 cm.

Fetal hemoglobin probe 115B includes light source 105, first detector 160A, second detector 160B, third detector 160C, a fourth detector 160D, and a fifth detector 160E positioned within a housing 102. In fetal hemoglobin probe 115B, first detector 160A and fourth detector 160D are positioned in a row that approximately aligns in the center of a horizontal axis between detectors 160A and 160D. An approximate distance between light source 105 and (as measured along a Y-axis bisecting a center of light source 105) and a center of the horizontal axis between first and fourth detectors 160A and 160D is 0.5-3 cm. Second detector 160B and fifth detector 160E are positioned in a row that approximately aligns in the center of a horizontal axis between detectors 160B and 160D. In most instances, the first and fourth detectors 160A and 160D and/or second and fifth detectors 160B and 160E will be the same distance from light source 105 (as shown in FIG. 2B) but this need not always be the case. For example, detector 160A may be 2 cm from light source 105 and detector 160B may be 4 cm from light source 105. An approximate distance between light source 105 and (as measured along a Y-axis bisecting a center of light source 105) and a center of the horizontal axis between second and fifth detectors 160B and 160E is 0.5-8 cm. Third detector 160C may be approximately 3-10 cm away from light source 105. In some instances, fetal hemoglobin probe 115 may include multiple light sources 105. In some embodiments, the number and/or configuration of the components of fetal hemoglobin probe 115A and/or 115B may be different than what is shown in FIGS. 2A and 2B. For example, fetal hemoglobin probe 115A and/or 115B may have multiple light sources 105, more detectors 160, and/or fewer detectors.

Detectors 160A-160E may be adapted to detect a light and/or optical signal emanating from the abdomen of a pregnant mammal. The detected optical signal may correspond to light projected by light source 105 and incident upon the pregnant mammal and/or the fetus. Detectors 160 and/or 160A-160E and convert this light signal into a digital and/or electronic signal (referred to herein as a "detected electronic signal"), which may be communicated to a receiver like receiver 145, a computer like computer 150, a processor like processor 604 and/or an on-board transceiver that may be capable of communicating the signal to the computer/processor.

The components of fetal hemoglobin probe 115 are arranged so that a first and second detector 160A and 160B, respectively, may be positioned approximately 1.5-4 cm (along the Y-axis) from the light source 105 and there may be a distance of approximately 1-4 cm (along the Y-axis) between them.

Due to their relatively close proximity to light source 105, the signals detected by first and/or fourth (when present) detector(s) 160A and 160D may detect a signal primarily generated by light reflected by the pregnant mammal, with little contribution from light incident upon the fetus, and these signals may be used to, for example, determine motion artifacts of the pregnant mammal, maternal photoplethysmogram information (e.g., photoplethysmogram variation), maternal heartbeat information, and so on. In embodiments where, for example, ICA is employed to isolate a fetal signal from a total signal, a signal from first detector 160A may be used to determine, for example, a first type of signal/information for the pregnant mammal (e.g., photoplethysmogram information) and fourth detector 160D may be used to determine a second type of signal/information for the pregnant mammal (e.g., motion artifact, maternal respiratory signal, or pregnant mammal heartbeat information). For purposes of the following discussion, the term respiration or respiratory is used to refer to the movement of a volume of gas into and out of the lungs, also known as ventilation.

In some circumstances, first and/or fourth detector(s) 160A and 160D may be smaller and/or relatively less sensitive (e.g., lower gain) than other detectors resident in housing 102. Even though first and/or fourth detector(s) 160A and 160D may be smaller and/or relatively less sensitive, it is expected that they will still detect a signal of adequate strength due, at least in part, on their respective relatively close proximity to the light source 105. Using detectors of smaller size/lower sensitivity for first and/or fourth detector(s) 160A and 160D may serve to, for example, reduce the cost of manufacturing fetal hemoglobin probe 102 and decrease the overall size of fetal hemoglobin probe 102, which may make wearing fetal hemoglobin probe 102 more comfortable for the pregnant mammal.

Because second and fifth detectors 160B and 160E are positioned further away from light source 105, a greater portion of a signal detected by these detectors (when compared to the signals detected by detectors 160A and 160D) may be incident upon the fetus. Stated differently, because the light incident upon the pregnant mammal's abdomen is expected to be more diffuse further away from the light source, a detector positioned further away from the light source may be expected to detect light incident upon a more diffuse area of the pregnant mammal's abdomen, including the fetus contained therein. Thus, it is likely that a greater proportion of the signals detected by second and fifth detectors 160B and 160E will be incident upon the fetus. This may result in detected electronic signal with a higher fetal/pregnant mammal ratio. The two signals detected by second and fifth detectors 160B and 160E may then be correlated with, for example, one another, a signal detected by first detector 160A, a signal detected by fourth detector 160D, and/or one or more secondary signals (e.g., fetal heartbeat) in order to, for example, amplify or otherwise strengthen the portion of the signal incident upon the fetus (fetal signal) and/or isolate the fetal signal from the total signal.

Third detector 160C may be of the same size and/or gain as second and/or fifth detectors 160C and/or 160E and, in other embodiments, may be larger in size and/or higher in gain so as to, for example, detect a signal of sufficient strength given its relative distance from light source 105.

A signal detected by fifth detector 160E may provide a signal with a higher fetal/pregnant mammal ratio when compared with the signals detected by first, second, fourth, and/or fifth detectors 160A, 160B, 160D, and/or 160E due, in part, to its proximity to light source 105.

In some embodiments, a detector 160 may be a sensitive camera adapted to capture small changes in fetal skin tone caused by changes in cardiovascular pressure as the fetus' heart beats. In these embodiments, fetal hemoglobin probe 115 may be in contact with the pregnant mammal's abdomen, or not, as this embodiment may be used to perform so-called contactless pulse oximetry. In these embodiments, light source(s) 105 of fetal hemoglobin probe 115 may be adapted to provide light (e.g., in the visible spectrum, near-infrared, etc.) directed toward the pregnant mammal's abdomen so that the detector 160 is able to receive light reflected by the pregnant mammal's abdomen and fetus. The reflected light captured by a detector 160A-160E in this embodiment may be communicated to computer 150 for processing so as to convert the images to a measurement of fetal hemoglobin oxygen saturation according to, for example, one or more of the processes described herein.

It will be appreciated that a fetal hemoglobin probe 115 may include any number of light sources and/or detectors. In some cases, more than one fetal hemoglobin probe 115 may be used. Additionally, or alternatively, a fetal hemoglobin probe 115 may be used in addition to an external light source 105 and/or detector 160.

Figure 3:
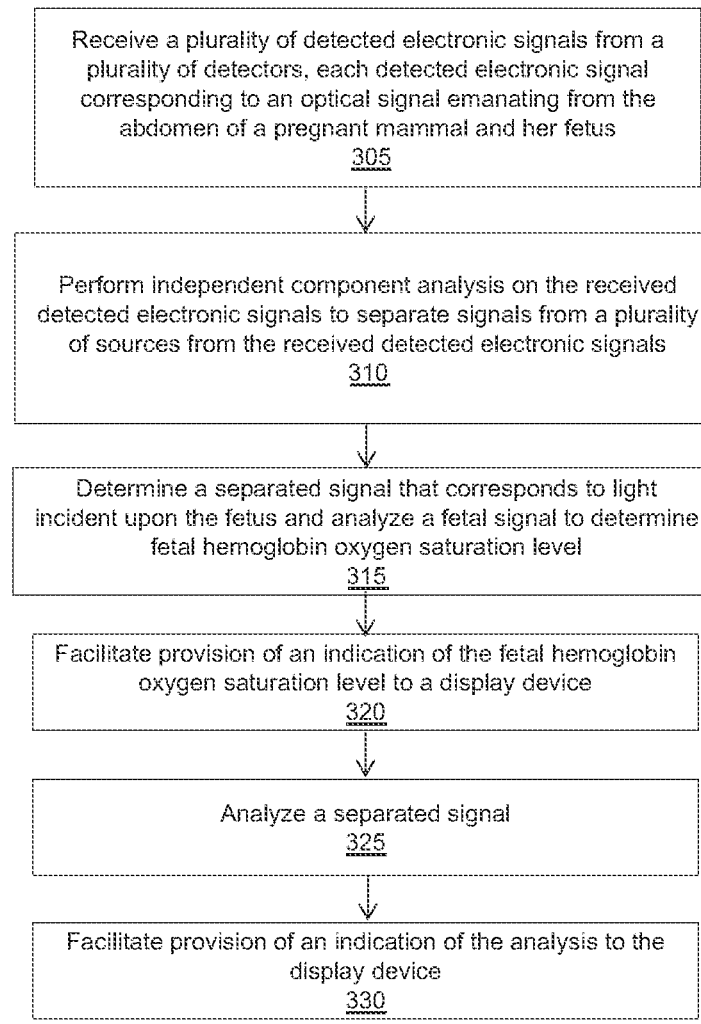
FIG. 3 is a flowchart illustrating an exemplary process for performing fetal oximetry and/or fetal pulse oximetry trans-abdominally and/or in-utero to determine fetal hemoglobin oxygen saturation level using independent component analysis, consistent with some embodiments of the present invention.

FIG. 3 provides a flowchart illustrating an exemplary process 300 for performing fetal oximetry and/or fetal pulse oximetry trans-abdominally and/or in-utero to determine fetal hemoglobin oxygen saturation level using independent component analysis. Process 300 may be performed by, for example, system 100 and/or a component thereof and/or a computer system like system 600 and/or a component thereof.

In step 305, a plurality of detected electronic signals may be received from a plurality (e.g., 3, 4, 5, 6, 7, 8, 9, etc.) of detectors, like detector 160, by a receiver such as receiver 145, and/or by a processor such as a processor 604. Each of the received detected electronic signals may correspond to an optical signal received by a detector included in the plurality of detectors, such as detectors 160A, 160B, 160C, 160D, or 160E that has been converted into a digital and/or electronic signal, which may be referred to herein as a "detected electronic signal." The optical signal received by each detector may correspond to an optical signal projected into the abdomen of the pregnant mammal from one or more light sources, like light source 105, that emanates (e.g., reflection, backscattering, and/or transmission) from the abdomen of the pregnant mammal and her fetus. The received detected electronic signals may include light or photons that have been incident upon one or more layers of maternal and/or fetal tissue. In addition, the detected electronic signals may include portions, or signals, that are contributed by different sources including, but not limited to, maternal respiration, maternal photoplethysmogram variation, uterine tone changes, fetal photoplethysmogram, noise, motion artifacts, etc.

Often times, the light directed into the pregnant mammal's abdomen and the fetus will be of at least two separate wavelengths and/or frequencies (e.g., red, infrared, near-infrared, etc.) and the received detected electronic signals may correspond to light of these different wavelengths. For example, in one embodiment, there may be five detectors present in a fetal hemoglobin probe, such as exemplary fetal hemoglobin probe 115A, as shown in FIG. 2 and discussed above. Light projected into the pregnant mammal's abdomen by, for example, light source 105, may emanate from the pregnant mammal's abdomen and fetus, and may be detected by one or more of detectors 160A-160E. The respective detector 160A-160E may then convert the light they detect into a detected electronic signal and these detected electronic signals may be received by, for example, a receiver like receiver 145, a processor like processor 604, and/or a computer like computer 150.

In step 310, independent component analysis (ICA) may be executed to separate multiple signals that may be included within one or more of the detected electronic signals received in step 305. Each of the signals that are separated by the ICA from the plurality of detected electronic signals may be generated by a different source that may be associated with, for example, the pregnant mammal's body, her fetus, or noise. Exemplary sources of the signals that may be separated by ICA include, but are not limited to, maternal respiration, maternal photoplethysmogram variations, fetal photoplethysmogram variations, uterine tone changes, and motion artifacts. Often times, the ICA may be performed to generate a separated signal for maternal respiration, a separated signal for maternal photoplethysmogram variations, a separated signal for fetal photoplethysmogram variations, and a separated signal for noise. It will be appreciated that the ICA may generate separated signals from a variety of sources that may be different from/interchanged with those described above. In some instances, the ICA may generate separate signals proportionally to the number of detected electronic signals it received (i.e., three detected electronic signals yields three separated signals; four detected electronic signals yields four separated signals, etc.).

In some embodiments, execution of step 310 may include using blind source separation to separate out the signals contributed by the different sources. Additionally, or alternatively, execution of the ICA may be based on, or otherwise include, a maximum likelihood estimation (MLE). An objective of the ICA may be to isolate a portion of the received detected electronic signals that corresponds to light that has been incident upon the fetus and/or isolate a fetal photoplethysmogram signal. At times, a portion of the detected received signals that corresponds to the light that has been incident upon and/or incident upon the fetus may be referred to herein as a "fetal signal."

Next, a separated signal associated with light that was incident upon the fetus (often times a fetal photoplethysmogram signal) may be analyzed to determine a fetal hemoglobin oxygen saturation level (step 315). In some embodiments, the fetal signal may correspond to the fetal photoplethysmogram signal. In some embodiments, execution of step 315 may include determining a ratio of a first wavelength of light (e.g., red light) included in the fetal signal and a second wavelength of light included in the fetal signal (e.g., near-infrared (NIR) light) and this ratio may be used to determine the fetal hemoglobin oxygen saturation level via known correlations between this ratio and the oxygen saturation of fetal hemoglobin via, for example, use of the Beer-Lambert Law and/or the Modified Beer-Lambert Law. Provision of the determined fetal hemoglobin oxygen saturation level to a user (e.g., doctor or nurse) may then be facilitated via, for example, communication of the fetal hemoglobin oxygen saturation level to a display device (e.g., display screen of a computer) like display device 155 (step 320). In some embodiments, step 320 may be performed by providing the user with a numerical value and/or graph showing the fetal hemoglobin oxygen saturation level and/or changes to fetal hemoglobin oxygen saturation level. Additionally, or alternatively, the fetal hemoglobin oxygen saturation level may be provided as a time weighted average taken over, for example, 30 seconds and/or 1, 2, 5, 10, 20, and/or 30 minutes.

Optionally, in some embodiments, one or more of the separated signals produced in step 310 may be analyzed (step 325) in order to, for example, monitor a source of the respective separated signal(s) under analysis. For example, if one of the signals separated in step 310 corresponds to a maternal respiratory signal, then this separated signal may be analyzed to determine one or more features of the pregnant mammal's breathing and/or respiratory cycle. Additionally, or alternatively, if one of the signals separated in step 310 corresponds to a uterine tone signal (which may indicate a muscular state of the uterus), then this separated signal may be analyzed to determine one or more features of the contractions and/or muscle tone of the pregnant mammal's uterus. Additionally, or alternatively, if one of the signals separated in step 310 corresponds to a maternal photoplethysmogram, then this separated signal may be analyzed to determine one or more features of the pregnant mammal's hemoglobin oxygen saturation. Then, results of this analysis may be provided to the user via, for example, communication of the results to a display device (step 330).

Figure 4:
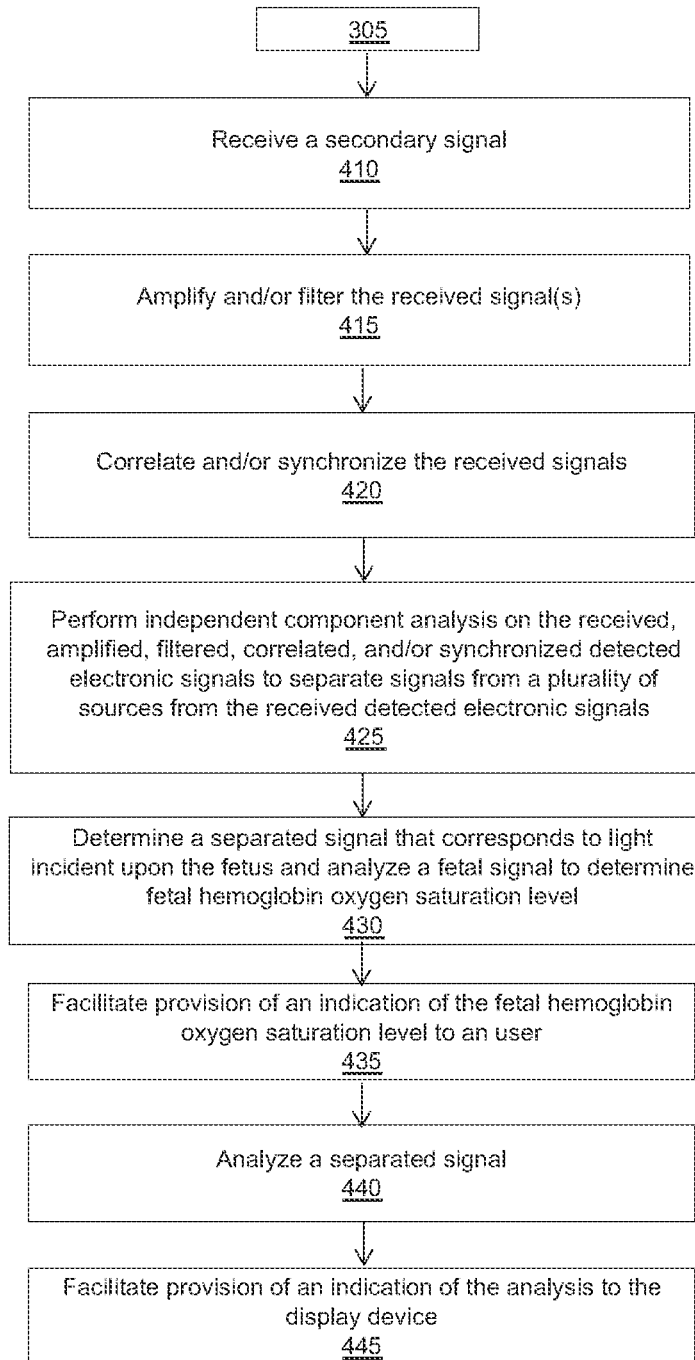
FIG. 4 is a flowchart illustrating an exemplary process for performing fetal oximetry and/or fetal pulse oximetry trans-abdominally and/or in-utero to determine fetal hemoglobin oxygen saturation level using independent component analysis, consistent with some embodiments of the present invention.

FIG. 4 provides a flowchart illustrating an exemplary process 400 for performing fetal oximetry and/or fetal pulse oximetry trans-abdominally and/or in-utero to determine fetal hemoglobin oxygen saturation level using independent component analysis. Process 400 may be performed by, for example, system 100 and/or a component thereof and/or a computer system like system 600 and/or a component thereof.

Initially, step 305 may be performed. Then, one or more secondary signal(s) may be received in step 410. In some instances, the secondary signals may be signals that are not detected optical signals or correlated to detected optical signals and, in other instances, the secondary signals may be derived from the detected optical signals. Exemplary secondary signals include, but are not limited to, a heartbeat signal for the pregnant mammal, as may be provided by an ECG device like ECG device 170, a heartbeat signal for the fetus, as may be provided by an ultrasound device Doppler/ultrasound probe 135, a pulse oximetry signal for the pregnant mammal as may be provided by a pulse oximetry probe like pulse oximetry probe 130, an indication of the pregnant mammal's hemoglobin oxygen saturation as may be provided by NIRS adult hemoglobin probe 125, and/or in indication of uterine tone and/or contractions as may be provided by uterine contraction measurement device.

In step 415, the signals received in step 305 and 410 may be amplified, filtered, or otherwise processed in order to, for example, reduce noise and/or amplify the signal, or portions thereof. In most instances, step 415 will be executed separately for each received signal. In some embodiments, execution of step 415 may include execution of known amplification and/or filtration techniques.

In some embodiments, execution of step 415 may include processing one or more of the signals received in step 305 with a secondary signal received in step 410. For example, if the secondary signal is a maternal heartrate signal (as may be received from, for example, ECG device 170), then the maternal heartrate signal may be used to determine which portions of the signals received in step 305 are contributed by the pregnant mammal. These portions may then be subtracted and/or divided from the signals received in step 305 to remove maternal contributions to the signals received in step 305. Additionally, or alternatively, if the secondary signal is a fetal heartrate signal, then the fetal heartrate signal may be used to determine which portions of the signals received in step 305 are contributed by the fetus because, for example, the oxygenation level of the fetus may fluctuate in a manner that corresponds to its pulse or heartrate. These portions of the signals received in step 305 may then be amplified by, for example, multiplying them by the fetal signal produced by subtracting portions of the maternal contributions from the signals received in step 305 and/or subtraction of portions of the signals received in step 305 that are not contributed by the fetus.

In other embodiments, the filtering of one or more of the received detected electronic signal(s) of step 415 may employ using one or more wavelet filters to filter the signal. Wavelet filters use a "mother wavelet" as the shape of the filter and, in order to improve the quality (e.g., signal-to-noise ratio) of a received signal, different mother wavelets (e.g., standard mother wavelets) may be used to optimize the signal being filtered. Additionally, or alternatively, a mother wavelet may be tailored to filter out portions of a received signal that may not correspond to the fetal signal, or what the fetal signal may be expected to be. An exemplary tailored, or specific, wavelet filter/mother wavelet may be derived from, for example, prototypical fetal signals that may be derived from, for example, fetal heartbeat signals (as provided by for example, Doppler/ultrasound probe 135), an arterial pressure sensor, or a fetal pulse oximetry signal. In some instances, this tailored, or specific, mother wavelet may be generated in real time (or near real time) as it is being used to filter one or more of the received detected electronic signals.

Additionally, or alternatively, filtering of one or more of the signals in step 415 may include evaluating the signal using undecimated and/or decimated multivariate empirical mode decomposition filter banks so as to, for example, create a filter tailored for a specific signal (e.g., the fetal signal, or a portion of the signal incident upon the pregnant mammal's breathing or uterine contractions).

Additionally, or alternatively, filtering and/or amplifying of one or more of the signals may include one or more of quantifying noise and other signal levels, evaluating fast Fourier transforms (FFTs), determining how harmonics and fetal signals overlap, removing motion artifacts (as may be caused by, for example, uterine contractions and/or maternal respiration), determining whether there is adequate optical signal amplitude, evaluating signals for sufficient signal amplitude, removal of portions of a signal that are below a quality (e.g., signal-to-noise ratio) threshold, and evaluating signals for sufficient signal capture length.

Additionally, or alternatively, filtering and/or amplifying of one or more of the signals may include one or more of creation of an ultrasound envelope corresponding to the arterial pressure pulse of the fetus, band pass filtering one or more of the signals to reduce portions of the respective signal received from non-fetal sources, detrending the received optical signals for breathing (of the pregnant mammal) and a DC signal generated transmission of light through tissue that does not correspond to arterial pulsatile blood flow, creating a blood pressure synchronous pulse signal using, for example, fetal heartbeat data and/or a fetal blood pressure data, calculating the amplitude of the correlation signal of two or more optical (e.g., light in the red, near-infrared, and/or infrared frequency/wavelength ranges) signals, normalizing an AC pulsatile signal to the DC level, determining a ratio between the two or more frequencies/wavelengths (e.g., a red light/infrared light ratio) of light included in a signal received in step 305, corresponds to light, and calibrating the determined ratio to a fetal blood oxygenation saturation level.

Optionally, in step 420, two or more of the received signals may be correlated to one another and/or synchronized in, for example, the time and/or frequency domains. The synchronization and/or correlation performed in step 420 may include gating a first of the two or more received signals so that it corresponds in time to a second of the two or more received signals. In this way events present in the received two or more received signals may align in time so that events of a first signal line up in time with the corresponding event in the second signal. In this way, when the first signal is used to understand the second signal (or vice versa), the first and second signals may be correlated in time.

In most instances, the correlation and/or synchronization of step 420 is performed by synchronizing one or more of the secondary signals received in step 410 with one or more of the signals received in step 305. For instance, execution of step 420 may involve synchronizing the one or more of the signals received in step 305 with a fetal heart beat signal and/or fetal blood pressure signal received in step 410. Additionally, or alternatively, execution of step 420 may involve performing a correlation function with one or more signals (individually or jointly) received in step 305 with a fetal heart beat signal and/or fetal blood pressure signal received in step 410.

Additionally, or alternatively, execution of step 420 may include correlating and/or synchronizing the detected optical signals received by the different detectors (e.g., detectors 160A-160E). At times, this step may not be necessary due to, for example, the speed of light and the relatively short distances between the light source(s) and the respective detectors.

In step 425, ICA may be performed on the received, amplified, filtered, correlated, and/or synchronized detected electronic signals to separate out signals contributed by different sources. Execution of step 425 may be similar to execution of step 310 with the exception that the input signal may be different. Instead of the input signal being the plurality of detected electronic signals received in step 305, the ICA of step 425 may be performed on amplified, filtered, correlated, and/or synchronized signals as may be generated by execution of step 415 and/or 420.

Next, the separated signals may be analyzed to determine a separated signal that corresponds to light incident upon the fetus (which may be referred to herein as a "fetal signal") and the fetal signal may be analyzed to determine a fetal hemoglobin oxygen saturation level (step 430). Often, execution of step 430 may resemble execution of step 315.

Provision of the determined fetal hemoglobin oxygen saturation level to a user (e.g., doctor or nurse) may then be facilitated via, for example, communication of the fetal hemoglobin oxygen saturation level to a display device (e.g., display screen of a computer) like display device 155 (step 435). In some embodiments, step 435 may be performed by providing the user with a numerical value and/or graph showing the fetal hemoglobin oxygen saturation level and/or changes to fetal hemoglobin oxygen saturation level. Additionally, or alternatively, the fetal hemoglobin oxygen saturation level may be provided as a time weighted average taken over, for example, 30 seconds and/or 1, 2, 5, 10, 20, and/or 30 minutes.

Optionally, in some embodiments, one or more of the separated signals produced in step 425 may be analyzed (step 440) in order to, for example, monitor a source of the respective separated signal(s) under analysis and results of this analysis may be provided to the user via, for example, communication of the results to a display device (step 445). Execution of steps 440 and 445 may resemble execution of steps 325 and 330, respectively.

Figure 5:
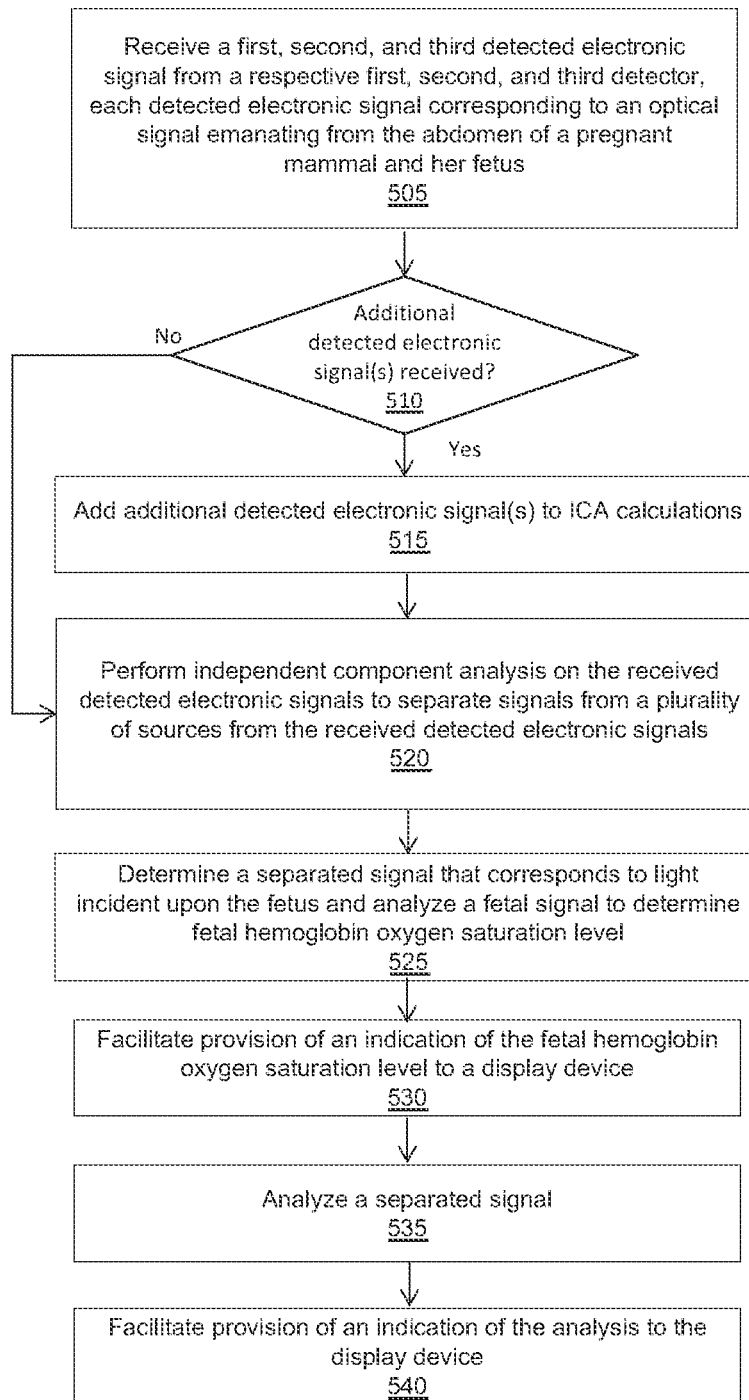
FIG. 5 is a flowchart illustrating an exemplary process for performing fetal oximetry and/or fetal pulse oximetry trans-abdominally and/or in-utero to determine fetal hemoglobin oxygen saturation level using independent component analysis, consistent with some embodiments of the present invention.

FIG. 5 provides a flowchart illustrating another exemplary process 500 for performing fetal oximetry and/or fetal pulse oximetry trans-abdominally and/or in-utero to determine fetal hemoglobin oxygen saturation level using independent component analysis. Process 500 may be performed by, for example, system 100 and/or a component thereof and/or a computer system like system 600 and/or a component thereof.

In step 505, a first detected electronic signal may be received from a first detector (e.g., detector 160A), a second electronic signal may be received from a second detector (e.g., detector 160B), and third detected electronic signal may be received a third detector (e.g., 160C) of fetal hemoglobin probe 115A or 115B. Each of the received detected electronic signals may correspond to an optical signal received by the respective first, second, and third detector that has been converted into a digital and/or electronic signal or detected electronic signal. The optical signal received by each detector may correspond to an optical signal projected into the abdomen of the pregnant mammal from one or more light sources, like light source 105, that emanates (e.g., reflection, backscattering, and/or transmission) from the abdomen of the pregnant mammal and her fetus. The received detected electronic signals may include light or photons that have been incident upon one or more layers of maternal and/or fetal tissue. In addition, the detected electronic signals may include portions, or signals, that are contributed by different sources including, but not limited to, maternal respiration, maternal photoplethysmogram variation, uterine tone changes, fetal photoplethysmogram, noise, motion artifacts, etc.

Often times, the light directed into the pregnant mammal's abdomen and the fetus will be of at least two separate wavelengths and/or frequencies (e.g., red, infrared, near-infrared, etc.) and the received detected electronic signals may correspond to light of these different wavelengths. For example, light projected into the pregnant mammal's abdomen by, for example, light source 105, may emanate from the pregnant mammal's abdomen and fetus, and may be detected by one or more of detectors 160A-160C. The respective detector 160A-160C may then convert the light they detect into a detected electronic signal and these detected electronic signals may be received by, for example, a receiver like receiver 145 and/or processor inside a computer like computer 150.

In step 510, it may be determined if additional (e.g., fourth, fifth, sixth, etc.) detected electronic signal(s) are received from additional detectors and, if so, the additional (e.g., fourth, fifth, sixth, etc.) detected electronic signal(s) may be added to the ICA calculations performed in step 520 (step 515). If not, process 500 proceeds to step 520.

In step 520, ICA may be executed to separate multiple signals that may be included within one or more of the detected electronic signals received in step 505. Each of the signals that are separated by the ICA from the plurality of detected electronic signals may be generated by a different source that may be associated with, for example, the pregnant mammal's body, her fetus, or noise. Exemplary sources of the signals that may be separated by ICA include, but are not limited to, maternal respiration, maternal photoplethysmogram variations, fetal photoplethysmogram variations, uterine tone changes, and motion artifacts. Often times, the ICA may be performed to generate a separated signal for maternal respiration, a separated signal for maternal photoplethysmogram variations, a separated signal for fetal photoplethysmogram variations, and a separated signal for noise. When only three detected electronic signals are received in step 505, the ICA may generate three separated signals. When additional detected electronic signals are received in step 510, the ICA may generate an additional separated signal for each additional detected electronic signal received.

In an embodiment where three detected electronic signals are received, the ICA may generate a first separated signal for maternal photoplethysmogram variations (source is maternal photoplethysmogram variations), a second separated signal for noise (source is noise), and a third separated signal for fetal photoplethysmogram variations (source is maternal photoplethysmogram variations). Alternatively, in some embodiments, the first or second separated signal may be for maternal respiration (source is maternal respiration) or uterine tone (source is maternal respiration). In embodiments where more than three detected electronic signals are received, a fourth separated signal may be for maternal respiration (source is maternal respiration) or uterine tone (source is changes in uterine tone). It will be appreciated that the ICA may generate separated signals from a variety of sources that may be different from/interchanged with those described above. In some instances, the ICA may generate separate signals proportionally to the number of detected electronic signals it received (i.e., three detected electronic signals yields three separated signals; four detected electronic signals yields four separated signals, etc.)

In some embodiments, execution of step 520 may include using blind source separation to separate out the signals contributed by the different sources. Additionally, or alternatively, execution of the ICA may be based on, or otherwise include, a maximum likelihood estimation (MLE). An objective of the ICA may be to isolate a portion of the received detected electronic signals that corresponds to light that has been incident upon the fetus and/or generate a separated fetal photoplethysmogram signal. At times, a portion of the detected received signals that corresponds to the light that has been incident upon and/or incident upon the fetus may be referred to herein as a "fetal signal."

Next, a separated signal associated with light that was incident upon the fetus (often times a fetal photoplethysmogram signal) may be analyzed to determine a fetal hemoglobin oxygen saturation level (step 525). In some embodiments, execution of step 525 may include determining a ratio of a first wavelength of light (e.g., red light) included in the fetal signal and a second wavelength of light included in the fetal signal (e.g., near-infrared (NIR) light) and this ratio may be used to determine the fetal hemoglobin oxygen saturation level via known correlations between this ratio and the oxygen saturation of fetal hemoglobin via, for example, use of the Beer-Lambert Law and/or the Modified Beer-Lambert Law. Provision of the determined fetal hemoglobin oxygen saturation level to a user (e.g., doctor or nurse) may then be facilitated via, for example, communication of the fetal hemoglobin oxygen saturation level to a display device (e.g., display screen of a computer) like display device 155 (step 530). In some embodiments, step 530 may be performed by providing the user with a numerical value and/or graph showing the fetal hemoglobin oxygen saturation level and/or changes to fetal hemoglobin oxygen saturation level. Additionally, or alternatively, the fetal hemoglobin oxygen saturation level may be provided as a time weighted average taken over, for example, 30 seconds and/or 1, 2, 5, 10, 20, and/or 30 minutes.

Optionally, in some embodiments, one or more of the separated signals produced in step 520 may be analyzed (step 535) in order to, for example, monitor a source of the respective separated signal(s) under analysis. For example, if one of the signals separated in step 520 corresponds to a maternal respiratory signal, then this separated signal may be analyzed to determine one or more features of the pregnant mammal's breathing and/or respiratory cycle. Additionally, or alternatively, if one of the signals separated in step 520 corresponds to a uterine tone signal (which may indicate a muscular state of the uterus), then this separated signal may be analyzed to determine one or more features of the contractions and/or muscle tone of the pregnant mammal's uterus. Additionally, or alternatively, if one of the signals separated in step 520 corresponds to a maternal photoplethysmogram, then this separated signal may be analyzed to determine one or more features of the pregnant mammal's hemoglobin oxygen saturation. Then, results of this analysis may be provided to the user via, for example, communication of the results to a display device (step 540).

Figure 6:
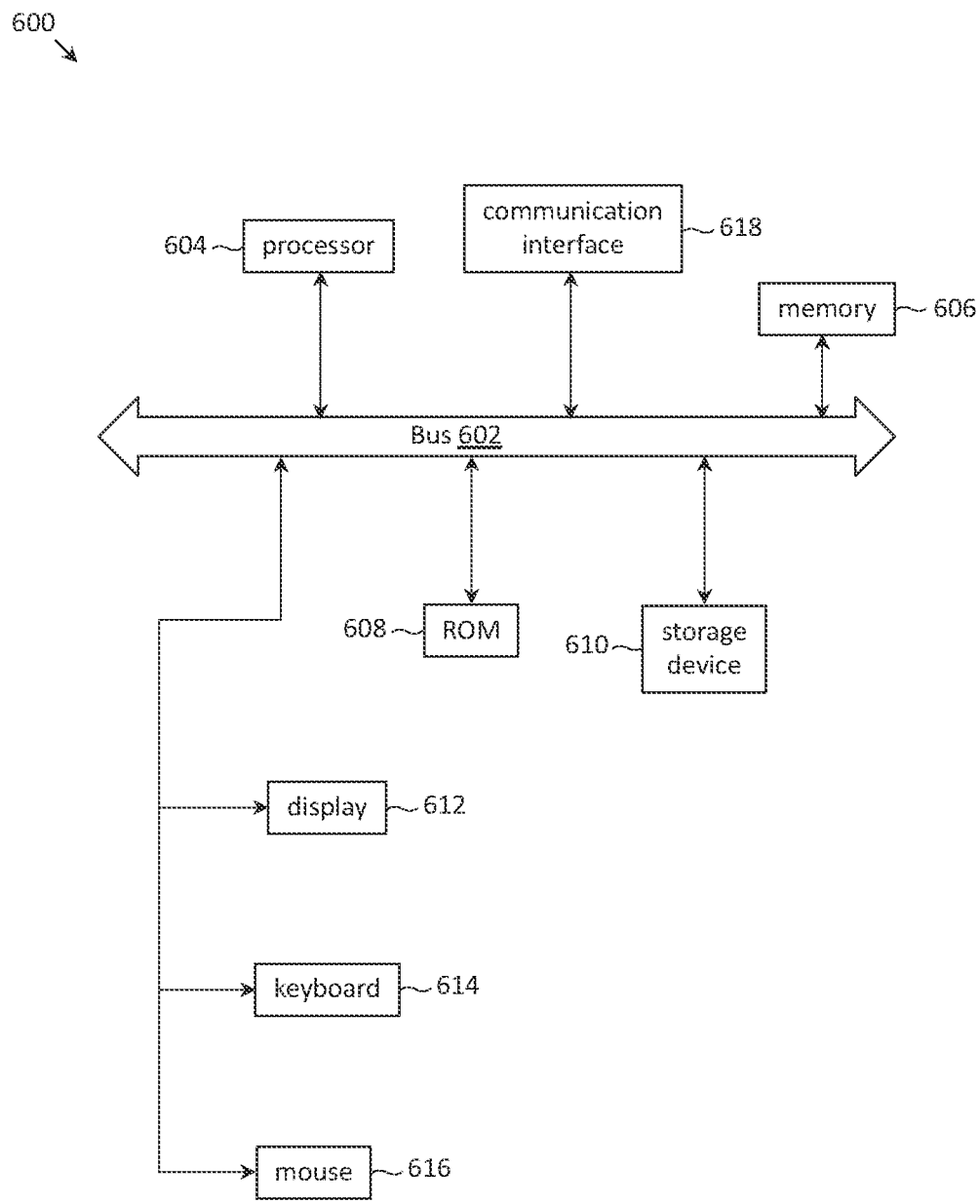
FIG. 6 depicts components of a computer system in which computer readable instructions instantiating the methods of the present invention may be stored and executed, consistent with some embodiments of the present invention.

FIG. 6 provide an example of a processor-based system 600 that may store and/or execute instructions for the processes described herein. Processor-based system 600 may be representative of, for example, computing device 150. Note, not all of the various processor-based systems which may be employed in accordance with embodiments of the present invention have all of the features of system 600. For example, certain processor-based systems may not include a display inasmuch as the display function may be provided by a client computer communicatively coupled to the processor-based system or a display function may be unnecessary. Such details are not critical to the present invention.

System 600 includes a bus 602 or other communication mechanism for communicating information, and a processor 604 coupled with the bus 602 for processing information. System 600 also includes a main memory 606, such as a random access memory (RAM) or other dynamic storage device, coupled to the bus 602 for storing information and instructions to be executed by processor 604. Main memory 606 also may be used for storing temporary variables or other intermediate information during execution of instructions to be executed by processor 604. System 600 further includes a read only memory (ROM) 608 or other static storage device coupled to the bus 602 for storing static information and instructions for the processor 604. A storage device 610, which may be one or more of a floppy disk, a flexible disk, a hard disk, flash memory-based storage medium, magnetic tape or other magnetic storage medium, a compact disk (CD)-ROM, a digital versatile disk (DVD)-ROM, or other optical storage medium, or any other storage medium from which processor 604 can read, is provided and coupled to the bus 602 for storing information and instructions (e.g., operating systems, applications programs and the like).

System 600 may be coupled via the bus 602 to a display 612, such as a flat panel display, for displaying information to a user. An input device 614, such as a keyboard including alphanumeric and other keys, may be coupled to the bus 602 for communicating information and command selections to the processor 604. Another type of user input device is cursor control device 616, such as a mouse, a trackball, or cursor direction keys for communicating direction information and command selections to processor 604 and for controlling cursor movement on the display 612. Other user interface devices, such as microphones, speakers, etc. are not shown in detail but may be involved with the receipt of user input and/or presentation of output.

The processes referred to herein may be implemented by processor 604 executing appropriate sequences of processor-readable instructions stored in main memory 606. Such instructions may be read into main memory 606 from another processor-readable medium, such as storage device 610, and execution of the sequences of instructions contained in the main memory 606 causes the processor 604 to perform the associated actions. In alternative embodiments, hard-wired circuitry or firmware-controlled processing units (e.g., field programmable gate arrays) may be used in place of or in combination with processor 604 and its associated computer software instructions to implement the invention. The processor-readable instructions may be rendered in any computer language.

System 600 may also include a communication interface 618 coupled to the bus 602. Communication interface 618 may provide a two-way data communication channel with a computer network, which provides connectivity to the plasma processing systems discussed above. For example, communication interface 618 may be a local area network (LAN) card to provide a data communication connection to a compatible LAN, which itself is communicatively coupled to other computer systems. The precise details of such communication paths are not critical to the present invention. What is important is that system 600 can send and receive messages and data through the communication interface 618 and in that way communicate with other controllers, etc.

Hence, systems, devices, and methods for determining fetal oxygen level have been herein disclosed. In some embodiments, use of the systems, devices, and methods described herein may be particularly useful during the labor and delivery of the fetus (e.g., during the first and/or second stage of labor).

We claim:

1. A method comprising:
receiving, by a processor, a plurality of detected electronic signals at least some of the plurality of detected electronic signals being contributed by different sources;
performing, by the processor, independent component analysis on the plurality of detected electronic signals to separate signals within the plurality of detected electronic signals into a plurality of separated signals, each of the separated signals included in the plurality of separated signals corresponding to a different source;
determining, by the processor, a separated signal that corresponds to light incident upon a fetus contained within an abdomen of a pregnant mammal;
analyzing, by the processor, the separated signal that corresponds to light incident upon the fetus to determine a fetal hemoglobin oxygen saturation level of the fetus; and
facilitating, by the processor, provision of an indication of the fetal hemoglobin oxygen saturation level to a user.

2. The method of claim 1, wherein the separated signal that corresponds to light incident upon the fetus is a fetal photoplethysmogram signal.

3. The method of claim 1, wherein the source of a separated signal is at least one of a maternal photoplethysmogram, a fetal photoplethysmogram, a maternal respiratory signal, a uterine tone signal, and a noise signal.

4. The method of claim 1, further comprising:
analyzing, by the processor, a separated signal that corresponds to light incident upon the pregnant mammal; and
facilitating, by the processor, provision of an indication of the analysis results to the user.

5. The method of claim 4, wherein the separated signal that corresponds to light incident upon the pregnant mammal is at least one of a maternal photoplethysmogram signal, a maternal respiratory signal, and a uterine tone signal.

6. The method of claim 1, further comprising:
filtering, by the processor, the received plurality of detected electronic signals prior to performance of the independent component analysis.

7. The method of claim 1, further comprising:
receiving, by the processor, a secondary signal; and
filtering, by the processor, the received plurality of detected electronic signals using the received secondary signal prior to performance of the independent component analysis.

8. The method of claim 7, further comprising:
synchronizing, by the processor, the secondary signal and the received plurality of detected electronic signals prior to filtering the received plurality of detected electronic signals.

9. A method comprising:
receiving, by a processor, a plurality of detected electronic signals;
receiving, by the processor, a secondary signal;
filtering, by the processor, the received plurality of detected electronic signals using the received secondary signal;
performing, by the processor, independent component analysis on the plurality of filtered detected electronic signals to separate signals within the detected electronic signals that are contributed by different sources, each of the separated signals corresponding to a different source;
determining, by the processor, a separated signal that corresponds to light incident upon a fetus contained within a pregnant mammal's abdomen;
analyzing, by the processor, the separated signal that corresponds to light incident upon the fetus to determine a fetal hemoglobin oxygen saturation level of the fetus; and
facilitating, by the processor, provision of an indication of the fetal hemoglobin oxygen saturation level to a user.

10. The method of claim 9, wherein the separated signal that corresponds to light incident upon the fetus is a fetal photoplethysmogram signal.

11. The method of claim 9, wherein the source of a separated signal is at least one of a maternal photoplethysmogram, a fetal photoplethysmogram, a maternal respiratory signal, a uterine tone signal, and a noise signal.

12. The method of claim 9, further comprising:
analyzing, by the processor, a separated signal that corresponds to light incident upon the pregnant mammal; and
facilitating, by the processor, provision of an indication of the analysis results to the user.

13. The method of claim 12, wherein the separated signal that corresponds to light incident upon the pregnant mammal is at least one of a maternal photoplethysmogram signal, a maternal respiratory signal, and a uterine tone signal.

14. The method of claim 9, further comprising:
amplifying, by the processor, the received plurality of detected electronic signals prior to performance of the independent component analysis.

15. The method of claim 9, further comprising:
synchronizing, by the processor, the secondary signal and the received plurality of detected electronic signals prior to filtering the received plurality of detected electronic signals.

16. A method comprising:
receiving, by a processor, a first detected electronic signal from a first detector, a second detected electronic signal from a second detector, and a third detected electronic signal from a third detector, each of the first, second, and third detectors being communicatively coupled to the processor and each of the first, second, and third detected electronic signals corresponding to a detected optical signal emanating from a pregnant mammal's abdomen and at least one of the first, second, and third detected electronic signals corresponding to a detected optical signal emanating from a pregnant mammal's abdomen also emanating from a fetus contained in the pregnant mammal's abdomen that is detected by the respective first, second, and third detectors and converted into the respective first, second, and third detected electronic signals;
performing, by the processor, independent component analysis on the first, second, and third detected electronic signals to generate a first separated signal, a second separated signal, and a third separated signal, the first separated signal, second separated signal, and third separated signal being contributed to the first, second, and third detected electronic signals by a first source, a second source, and a third source, respectively, wherein the third separated signal corresponds to a fetal photoplethysmogram signal;
analyzing, by the processor, the third separated signal to determine a hemoglobin oxygen saturation level of the the fetus contained within the pregnant mammal's abdomen; and
facilitating, by the processor, provision of an indication of the hemoglobin oxygen saturation level of the fetus to a user.

17. The method of claim 16, wherein the first source of the first separated signal is at least one of motion artifacts of the pregnant mammal, respiration of the pregnant mammal, photoplethysmogram variations of the pregnant mammal, uterine tone of the pregnant mammal, and noise.

18. The method of claim 16, wherein the second source of the second separated signal is at least one of motion artifacts of the pregnant mammal, respiration of the pregnant mammal, photoplethysmogram variations of the pregnant mammal, uterine tone of the pregnant mammal, and noise.

19. The method of claim 16, further comprising:
receiving, by the processor, a fourth detected electronic signal from a fourth detector communicatively coupled to the processor prior to performance of the independent component analysis, the fourth detected electronic signal corresponding to a detected optical signal emanating from the pregnant mammal's abdomen and fetus contained that is detected by the fourth detector and converted into the fourth detected electronic signal therein, wherein the independent component analysis is performed on the first, second, third, and fourth detected electronic signals to generate the first separated signal, the second separated signal, the third separated signal, and a fourth separated signal, the fourth separated signal being contributed by a fourth source.

20. A system comprising:
a processor, the processor adapted to:
receive a plurality of detected electronic signals;
perform independent component analysis on the plurality of detected electronic signals to separate signals within the detected electronic signals that are contributed by different sources, each of the separated signals corresponding to a different source;
determine a separated signal that corresponds to light incident upon a fetus contained within an abdomen of a pregnant mammal;
analyze the separated signal that corresponds to light incident upon the fetus to determine a fetal hemoglobin oxygen saturation level of the fetus; and facilitate provision of an indication of the fetal hemoglobin oxygen saturation level to a user.

21. The system of claim 20, wherein each of the plurality of detected electronic signals is received from a separate detector communicatively coupled to the processor and corresponding to a detected optical signal emanating from the pregnant mammal's abdomen and the fetus contained therein, wherein each detected optical signal has been converted, by the respective detector, into one of the plurality of the detected electronic signals.

22. The system of claim 21, wherein the optical signal includes at least two different wavelengths of light.

23. The system of claim 20, wherein the separated signal that corresponds to light incident upon the fetus is a fetal photoplethysmogram signal.

24. The system of claim 20, wherein the source of a separated signal is at least one of a maternal photoplethysmogram, a fetal photoplethysmogram, a maternal respiratory signal, a uterine tone signal, and a noise signal.

25. The system of claim 24, wherein the separated signal that corresponds to light incident upon the pregnant mammal is at least one of a maternal photoplethysmogram signal, a maternal respiratory signal, and a uterine tone signal.

26. The system of claim 20, wherein the processor is further adapted to:
analyze a separated signal that corresponds to light incident upon the pregnant mammal; and
facilitate provision of an indication of the analysis results to the user.

27. The system of claim 20, wherein the processor is further adapted to:
filter the received plurality of detected electronic signals prior to performance of the independent component analysis.

28. The system of claim 20, wherein the processor is further adapted to:
receive a secondary signal; and
filter the received plurality of detected electronic signals using the received secondary signal prior to performance of the independent component analysis.

29. The system of claim 28, wherein the processor is further adapted to:
synchronize the secondary signal and the received plurality of detected electronic signals prior to filtering the received plurality of detected electronic signals.

* * * * *